(12) United States Patent
Pellicciari

(10) Patent No.: US 9,540,414 B2
(45) Date of Patent: Jan. 10, 2017

(54) TGR5 MODULATORS AND METHODS OF USE THEREOF

(71) Applicant: Intercept Pharmaceuticals, Inc., New York, NY (US)

(72) Inventor: Roberto Pellicciari, Perugia (IT)

(73) Assignee: Intercept Pharmaceuticals, Inc., New York, NY (US)

( * ) Notice: Subject to any disclaimer, the term of this patent is extended or adjusted under 35 U.S.C. 154(b) by 0 days.

(21) Appl. No.: 14/449,995

(22) Filed: Aug. 1, 2014

(65) Prior Publication Data

US 2016/0052956 A1    Feb. 25, 2016

Related U.S. Application Data

(63) Continuation of application No. 13/056,797, filed as application No. PCT/US2009/052290 on Jul. 30, 2009, now Pat. No. 8,796,249.

(30) Foreign Application Priority Data

Jul. 30, 2008 (EP) .................................. 08013676

(51) Int. Cl.
    C07J 31/00      (2006.01)
    C07J 9/00       (2006.01)
    A61K 31/575     (2006.01)

(52) U.S. Cl.
    CPC ............ *C07J 31/006* (2013.01); *A61K 31/575* (2013.01); *C07J 9/00* (2013.01); *C07J 31/00* (2013.01)

(58) Field of Classification Search
    CPC ............ C07J 9/00; C07J 31/00; A61K 31/575
    USPC .................. 514/182; 552/542, 543, 551, 552
    See application file for complete search history.

(56) References Cited

U.S. PATENT DOCUMENTS

| | | | |
|---|---|---|---|
| 4,892,868 A | 1/1990 | Castagnola et al. | |
| 4,921,848 A | 5/1990 | Frigerio et al. | |
| 5,061,701 A | 10/1991 | Pellicciari et al. | |
| 5,128,481 A | 7/1992 | Oda et al. | |
| 5,175,320 A | 12/1992 | Pellicciari et al. | |
| 6,200,998 B1 | 3/2001 | Sahoo et al. | |
| 6,559,188 B1 | 5/2003 | Gatlin et al. | |
| 6,639,078 B1 | 10/2003 | Haffner et al. | |
| 6,777,446 B2 | 8/2004 | Houze et al. | |
| 6,906,057 B1 | 6/2005 | Forman et al. | |
| 6,984,650 B2 | 1/2006 | Haffner et al. | |
| 6,987,121 B2 | 1/2006 | Kliewer et al. | |
| 7,138,390 B2 | 11/2006 | Pellicciari | |
| 8,546,365 B2 | 10/2013 | Pellicciari et al. | |
| 2002/0094977 A1 | 7/2002 | Robl et al. | |
| 2002/0120137 A1 | 8/2002 | Houze et al. | |
| 2002/0132223 A1 | 9/2002 | Forman et al. | |
| 2003/0130296 A1 | 7/2003 | Bauer et al. | |

FOREIGN PATENT DOCUMENTS

| | | |
|---|---|---|
| EP | 0101554 A2 | 2/1984 |
| EP | 0124068 A1 | 11/1984 |
| EP | 0135782 A2 | 4/1985 |
| EP | 0186023 A2 | 7/1986 |
| EP | 0312867 A1 | 4/1989 |
| EP | 0393493 A2 | 10/1990 |
| EP | 1137940 A1 | 10/2001 |
| EP | 1140079 A1 | 10/2001 |
| EP | 1165135 A1 | 1/2002 |
| EP | 1185277 A1 | 3/2002 |
| EP | 1378749 A1 | 1/2004 |
| EP | 1473042 A1 | 11/2004 |
| EP | 1536812 A2 | 6/2005 |
| EP | 1568706 A1 | 8/2005 |
| EP | 1947108 A1 | 7/2008 |
| WO | WO9728149 A1 | 8/1997 |
| WO | WO9731907 A1 | 9/1997 |
| WO | WO9736579 A1 | 10/1997 |
| WO | WO9802159 A1 | 1/1998 |
| WO | WO9938845 A1 | 8/1999 |
| WO | WO0025134 A1 | 5/2000 |
| WO | WO0037077 A1 | 6/2000 |
| WO | WO0040965 A1 | 7/2000 |
| WO | WO0057915 A1 | 10/2000 |
| WO | WO0076523 A1 | 12/2000 |
| WO | WO0130343 A1 | 5/2001 |
| WO | WO0220463 A2 | 3/2002 |

(Continued)

OTHER PUBLICATIONS

Aldini et al. "Relationship between Structure and Intestinal Absorption of Bile Acids with a Steroid or Side-Chain Modification," Steroids 61:590-597 (1996).

Anderson et al. "Study of bile salt evolution including techniques for small-scale identification and their application to amphibian biles," Biochemical Journal vol. 141(2):485-494 (1974).

Bishop-Bailey et al., "Expression and activation of the farnesoid X receptor in the vasculature," Proc. Natl. Acad. Sci. U.S.A. 101(10):3668-3673 (2004).

(Continued)

*Primary Examiner* — Barbara P Badio
(74) *Attorney, Agent, or Firm* — Michelle Iwamoto-Fan

(57) ABSTRACT

The invention relates to compounds of Formula A:

(A)

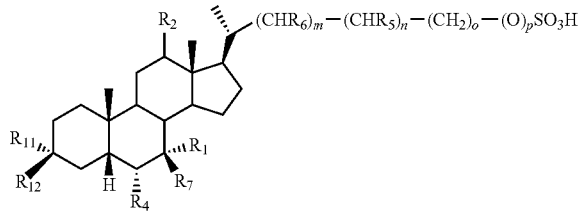

or a salt, solvate, or hydrate thereof. The compounds of formula A are TGR5 modulators useful for the treatment of disease.

2 Claims, 12 Drawing Sheets

(56) References Cited

FOREIGN PATENT DOCUMENTS

| | | |
|---|---|---|
| WO | WO02064125 A2 | 8/2002 |
| WO | WO02072598 A1 | 9/2002 |
| WO | WO03015771 A1 | 2/2003 |
| WO | WO03015777 A1 | 2/2003 |
| WO | WO03016280 A1 | 2/2003 |
| WO | WO03016288 A1 | 2/2003 |
| WO | WO03030612 A2 | 4/2003 |
| WO | WO03043581 A2 | 5/2003 |
| WO | WO03080803 A2 | 10/2003 |
| WO | WO03086303 A2 | 10/2003 |
| WO | WO03090745 A1 | 11/2003 |
| WO | WO2004007521 A2 | 1/2004 |
| WO | WO2004048349 A1 | 6/2004 |
| WO | WO2005032549 A1 | 4/2005 |
| WO | WO2005082925 A2 | 9/2005 |
| WO | WO2005089316 A2 | 9/2005 |
| WO | WO2006122977 A2 | 11/2006 |
| WO | WO2008002573 A2 | 1/2008 |
| WO | WO2008091540 A2 | 7/2008 |
| WO | WO2010059853 A1 | 5/2010 |

OTHER PUBLICATIONS

Center, S.A., et al., "Chronic Liver Disease: Current Concepts of Disease Mechanisms," J. Small Anim. Pract. 40(3):106-114 (1999).

Clerici et al. "Effect of Intraduodenal Administration of 23-Methyl-UDCA Diastereoisomers on Bile Flow in Hamsters," Digestive Diseases and Sciences 37(5):791-798 (1992).

Downes, M., et al., "A Chemical Genetic and Structural Analysis of the Nuclear Bile Acid Receptor FXR," Mol. Cell. 11(4) 1079-1092 (2003).

Fiorucci et al., "The Nuclear Receptor SHP Mediates Inhibition of Hepaptic Stellate Cells by FXR and Protects Against Liver Fibrosis," Gastroenterology 127:1497-1512 (2004).

Forman et al., "Identification of a Nuclear Receptor That Is Activated by Farnesol Metabolites," Cell 81:687-693 (1995).

Fukuchi et al., "5beta-Cholane activators of the farnesol X receptor," Journal of Steroid Biochemistry and Molecular Biology 94(4):311-318 (2005).

Haslewood et al., "Specificity and some characteristics of a 7.alpha.-hydroxysteroid dehydrogenase from E. coli," Datebase CA [online] Database accession No. 1978:419015.

Honório et al. "Hologram QSAR Studies on Farnesoid X Receptor Activators," Letters in Drug Design & Discovery 3:261-267 (2006).

Kihira et al., "Synthesis of sulfonate analogs of bile acids," Steroids 57(4):193-198 (1992).

Kim et al., "Hypocholesterolemic effect of bile acid sulfonate analogs in hamsters," Biological & Pharmaceutical Bulletin 24(3):218-220 (2001).

Kliewer et al., "Peroxisome Proliferator-Activated Receptors: From Genes to Physiology," Endo J. 56:239-263 (2001).

Liu, Y. et al., "Hepatoprotection by the Farnesoid X Receptor Agonist GW4064 in Rat Models of Intra- and Extrahepatic Cholestasis," J. Clin. Invest. 112(11) 1678-1687 (2003).

Mangelsdorf et al., "The RXR Heterodimers and Orphan Receptors," Cell 83:841-850 (1995).

Mi et al., "Structural Basis for Bile Acid Binding and Activation of the Nuclear Receptor FXR," Mol. Cell 11:1093-1100 (2003).

Mikami et al., "Effect of some sulfonate analogs of ursodeoxycholic acid on biliary lipid secretion in the rat," Journal of Lipid Research: 37(6):1181-1188 (1996).

Miki et al. "Sulfonate analogs of chenodeoxycholic acid: metabolism of sodium 3.alpha.,7.alpha.-dihydroxy-25-homo-5. beta.-cholane-25-sulfonate and sodium 3.alpha.7. alpha-dihydroxy-24-nor-5. beta.-cholane-23-sulfonate in the hamster," Journal of Lipid Research 33(11):1629-1637 (1992).

Nesto et al., "Thiazolidinedione Use Fluid Retention and Congestive Heart Failure," Diabetes Care 27(1):256-263 (2004).

Pellicciari et al., "6α-Ethyl-Chenodeoxycholic Acid (6-ECDCA) a Potent and Selective FXR Agonist Endowed with Anticholestatic Activity," J. Med. Chem. 45(17):3569-3572 (2002).

Pellicciari et al., "Bile Acid Derivatives as Ligands of the Farnesoid X Receptor. Synthesis Evaluation and Structure—Activity Relationship of a Series of Body and Side Chain Modified Analogues of Chenodeoxycholic Acid, " J. Med. Chem. 47:4559-4569 (2004).

Pellicciari et al., "Discovery of 6α-Ethyl-23(S)-methylcholic Acid (S-EMCA INT-777) as a Potent and Selective Agonist for the TGR5 Receptor a Novel Target for Diabesity," J. Med. Chem. 52:7958-7961 (2009).

Pellicciari et al., "Nongenomic actions of bile acids. Synthesis and preliminary characterization of 23- and 6 23-alkyl-substituted bile acid derivates as selective modulators for the G-Protein coupled receptor TGR5," Journal of Medicinal Chemistry 50(18): 4265-4268 (2007).

Raskin et al., "A Randomized Trial of Rosiglitazone Therapy in Patients With Inadequately Controlled Insulin-Treated Type 2 Diabetes," Diabetes Care 24(7):1226-1232 (2001).

Roda et al. "23-Methyl-3α,7β-dihydroxy-5β-cholan-24-oic Acid: Dose-Response Study of Biliary Secretion in Rat," Hepatology 8(6):1571-1576 (1988).

Roda et al., "Bile Acids with a Cyclopropyl-containing Side Chain. IV. Physiochemical and Biological Properties of the Four Diastereoisomers of 3α, 7β-dihydroxy-22 23-methylene-5β-cholan-24-oic Acid," Journal of Lipid Research 28:1384-1397 (1987).

Rubin et al., "Combination Therapy With Pioglitazone and Insulin in Patients With Type 2 Diabetes," Diabetes 48(Suppl. 1):A110 (1999) (Abstract Only).

Sato et al., "Novel Potent and Selective Bile Acid Derivatives as TGR5 Agonists: Biological Screening Structure-Activity Relationships and Molecular Modeling Studies," J.Med. Chem. 51:1831-1841 (2008).

Schmider et al. "Evidence for an additional sinusoidal bile salt transport system," Datebase CA [online]. Database accession No. 2000:260886 Feb. 16, 2009.

Souillac et al., "Characterization of Delivery Systems Differential Scanning Calorimetry," in Encyclopedia of Controlled Drug Delivery John Wiley & Sons pp. 212-227 (1999).

Stenner et al., "The effect of ursodeoxycholic acid on fibrosis markers in alcoholic liver disease," Flak Symposium pp. 229-235 (2002).

Urizar, N.L. et al., "A Natural Product that Lowers Cholesterol as an Antagonist Ligand for FXR," Science 296(5573):1703-1706 (2002).

Vippagunta et al., "Crystalline solids," Adv. Drug Del. Rev. 48:3-26 (2001).

Willson et al., "The PPARs: From Orphan Receptors to Drug Discovery," J. Med. Chem. 43(4):527-550 (2000).

Hiroyuki, Sato et al., "Novel Potent and Selective Bile Acid Derivatives as TGR5 Agonists: Biological Screening, Structure Activity Relationships, and Molecular Modeling Studies", J. Med. Chem., vol. 51, pp. 1831-1841, Feb. 29, 2008.

TGR5 MODULATORS AND METHODS OF USE THEREOF

RELATED APPLICATIONS

This application is a continuation of U.S. Ser. No. 13/056,797, filed on Mar. 22, 2011, now U.S. Pat. No. 8,796,249, which is a national stage application of International Application No. PCT/US2009/052290, filed on Jul. 30, 2009, which claims priority to EP Application No. 08013676.5, filed on Jul. 30, 2008, the contents of each of which are incorporated by reference in their entirety.

FIELD OF THE INVENTION

The invention concerns relates to compounds containing a sulfate or sulfonic acid moiety that modulate TGR5 and pharmaceutical compositions containing such compounds useful in methods for the treatment and prevention of disease.

BACKGROUND OF THE INVENTION

TGR5 receptor is a G-protein-coupled receptor that has been identified as a cell-surface receptor that is responsive to bile acids (BAs). The primary structure of TGR5 and its responsiveness to bile acids has been found to be highly conserved in TGR5 among human, bovine, rabbit, rat, and mouse, and thus suggests that TGR5 has important physiological functions. TGR5 has been found to be widely distributed in not only lymphoid tissues but also in other tissues. High levels of TGR5 mRNA have been detected in placenta, spleen, and monocytes/macrophages. Bile acids have been shown to induce internalization of the TGR5 fusion protein from the cell membrane to the cytoplasm. Kawamata et al. 2003, J. Bio. Chem., 278, 9435. TGR5 has been found to be identical to hGPCR19 reported by Takeda et al. 2002, FEBS Lett. 520, 97-101.

TGR5 is associated with the intracellular accumulation of cAMP, that is widely expressed in diverse cell types. While the activation of this membrane receptor in macrophages decreases pro-inflammatory cytokine production, (Kawamata, Y.; Fujii, R.; Hosoya, M.; Harada, M.; Yoshida, H.; Miwa, M.; Fukusumi, S.; Habata, Y.; Itoh, T.; Shintani, Y.; Hinuma, S.; Fujisawa, Y.; Fujino, M., A G protein-coupled receptor responsive to bile acids. J. Biol. Chem. 2003, 278, 9435-9440) the stimulation of TGR5 by BAs in adipocytes and myocytes enhances energy expenditure (Watanabe, M.; Houten, S. M.; Mataki, C.; Christoffolete, M. A.; Kim, B. W.; Sato, H.; Messaddeq, N.; Harney, J. W.; EZaki, 0.; Kodama, T.; Schoonjans, K.; Bianco, A. C.; Auwerx, J., Bile acids induce energy expenditure by promoting intracellular thyroid hormone activation. Nature. 2006, 439, 484-489). This latter effect involves the cAMP-dependent induction of type 2 iodothyronine deiodinase (D2), which by, locally converting T4 into T3, gives rise to increased thyroid hormone activity. Consistent with the role of TGR5 in the control of energy metabolism, female TGR5 knock-out mice show a significant fat accumulation with body weight gain when challenged with a high fat diet, indicating that the lack of TGR5 decreases energy expenditure and elicits obesity (Maruyama, T.; Tanaka, K.; Suzuki, J.; Miyoshi, H.; Harada, N.; Nakamura, T.; Miyamoto, Y.; Kanatani, A.; Tamai, Y., Targeted disruption of G protein-coupled bile acid receptor 1 (Gpbar1/MBar) in mice. J. Endocrinol. 2006, 191, 197-205). In addition and in line with the involvement of TGR5 in energy homeostasis, bile acid activation of the membrane receptor has also been reported to promote the production of glucagon-like peptide 1 (GLP-1) in murine enteroendocrine cell lines (Katsuma, S.; Hirasawa, A.; Tsujimoto, G., Bile acids promote glucagon-like peptide-1 secretion through TGR5 in a murine enteroendocrine cell line STC-1. Biochem. Biophys. Res. Commun. 2005, 329, 386-390). On the basis of all the above observations, TGR5 is an attractive target for the treatment of disease.

Few examples of TGR5 agonists have been so far described in literature. Recently, 23-alkyl-substituted and 6,23-alkyl-disubstituted derivatives of chenodeoxycholic acid, such as the 6β-ethyl-23(S)-methyl-chenodeoxycholic acid shown below, have been reported as potent and selective agonists of TGR5 (Pellicciari, R.; Sato, H.; Gioiello, A.; Costantino, G.; Macchiarulo, A.; Sadeghpour, B. M.; Giorgi, G.; Schoonjans, K.; Auwerx, J., Nongenomic actions of bile acids. Synthesis and preliminary characterization of 23- and 6,23-alkyl-substituted bile acid derivatives as selective modulators for the g-protein coupled receptor TGR5. J. Med. Chem. 2007, 50, 4265-4268).

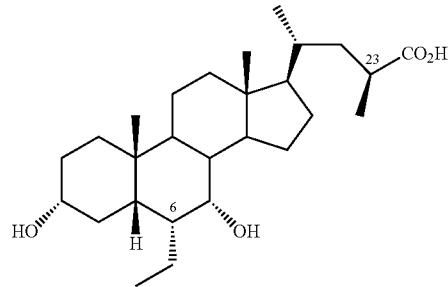 [SMILES: CC[C@H]1[C@@H](O)C2C3CC[C@H]([C@H](C)C[C@H](C)C(=O)O)[C@@]3(C)CCC2[C@@]2(C)CC[C@@H](O)C[C@@H]12]

In particular, methylation at the $C_{23}$—(S) position of natural BAs confers a marked selectivity to TGR5 over FXR (farnesoid X receptor) activation, whereas the 6α-alkyl substitution increases the potency at both receptors. Other TGR5 agonists include 6-methyl-2-oxo-4-thiophen-2-yl-1,2,3,4-tetrahydro-pyrimidine-5-carboxylic acid benzyl ester (WO004067008, Takeda Chemical Industries LTD, Japan, 2004) and oleanoic acid (Sato, H.; Genet, C.; Strehle, A.; Thomas, C.; Lobstein, A.; Wagner, A.; Mioskowski, C.; Auwerx, J.; Saladin, R., Anti-hyperglycemic activity of a TGR5 agonist isolated from Olea europaea. Biochem. and Biophys. Rev. Commun. 2007, 362, 793-798; Ito, F.; Hinuma, K.; Kanzaki, N.; Miki, T.; Kawamata, Y.; 0i, S.; Tawaeaishi, T.; Ishichi, Y.; Hirohashi, M. Preparation of aromatic ring-fused cyclic compounds as TGR5 receptor agonists. PN: WO2004067008, 2004. More recently, the first synthesis of enantiomeric chenodeoxycholic acid (CDCA) and lithocholic acid (LCA) has allowed to assess the specificity of the interaction of natural BAs to TGR5 (Katona, B. W.; Cummins, C. L.; Ferguson, A. D.; Li, T.; Schmidt, D. R.; Mangelsdorf, D. J.; Covey, D. F., Synthesis, Characterization, and Receptor Interaction Profiles of Enantiomeric Bile Acids. J. Med. Chem. 2007, 50, 6048-6058).

While these chemical tools have provided for the first time a pharmacological differentiation of genomic versus nongenomic effects of BAs, some of them also allowed to draw a first structure-activity relationship study where the presence of an accessory binding pocket in TGR5 plays a pivotal role in determining ligand selectivity (Pellicciari, R.; Sato, H.; Gioiello, A.; Costantino, G.; Macchiarulo, A.; Sadeghpour, B. M.; Giorgi, G.; Schoonjans, K.; Auwerx, J., Nongenomic actions of bile acids. Synthesis and preliminary characterization of 23- and 6,23-alkyl-substituted bile acid derivatives as selective modulators for the g-protein coupled receptor TGR5. *J. Med. Chem.* 2007, 50, 4265-4268). In this context, the availability of more potent and selective TGR5 modulators is necessary to further identify additional features affecting receptor activation and characterize the physiological and pharmacological actions of this receptor.

There is a need for the development of TGR5 modulators for the treatment and prevention of disease. The present invention has identified compounds, which contain a sulfate or sulfonic acid moiety, that modulate TGR5 as well as methods of using these compounds to treat disease.

SUMMARY OF THE INVENTION

The present invention relates to TGR5 modulators containing a sulfate or sulfonic acid moiety and their use to treat and prevent diseases that involve modulation of the TGR5 receptor, such as metabolic disease, inflammatory disease, liver disease, autoimmune disease, cardiac disease, kidney disease, cancer and gastrointestinal disease.

The invention includes a compound having the formula A:

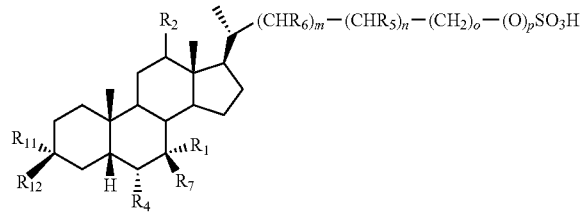

(A)

or a salt, solvate, or hydrate thereof, wherein $R_1$ is hydrogen, hydroxy, substituted or unsubstituted alkyl, or halogen; $R_2$ is hydrogen or α-hydroxy; $R_4$ is hydrogen, substituted or unsubstituted alkyl, or halogen; $R_5$ is hydrogen, unsubstituted alkyl, or aryl;

$R_6$ is hydrogen, unsubstituted or substituted alkyl, or $R_5$ and $R_6$ taken together with the carbons to which they are attached form a ring of size 3, 4, 5, or 6 atoms; $R_7$ is hydrogen, substituted or unsubstituted alkyl, or hydroxy; $R_{11}$ is hydroxyl, $OSO_3H$, $OSO_3^-$, $OCOCH_3$, $OPO_3H$, $OPO_3^{2-}$ or hydrogen; $R_{12}$ is hydroxyl, $OSO_3H$, $OSO_3^-$, $OCOCH_3$, $OPO_3H$, $OPO_3^{2-}$ or hydrogen, or taken together $R_{11}$ and $R_{12}$ form a carbonyl;

m is 0, 1 or 2; n is 0 or 1; o is 0, or 1; and p is 0 or 1; provided that (1) when m+n+o=3 or 4, p is zero, and $R_5$ is hydrogen, then $R_4$ is not hydrogen, unless $R_7$ is OH; (2) when m+n+o=3, p is 1, and $R_5$ and $R_6$ are each hydrogen, then at least one of $R_2$ and $R_4$ is not hydrogen; and (3) when m+n+o=2, then at least one of $R_5$ and $R_6$ is not hydrogen.

In one aspect, the invention includes a compound having the formula D:

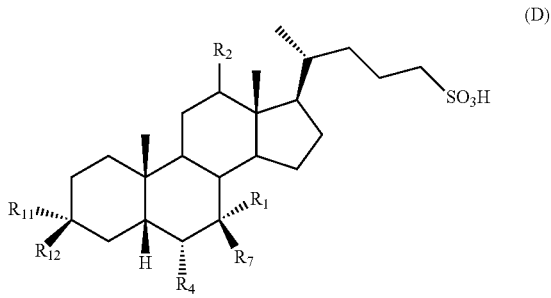

(D)

or a salt, solvate, or hydrate thereof, wherein $R_1$ is hydrogen, hydroxy, substituted or unsubstituted alkyl, or halogen; $R_2$ is hydrogen or α-hydroxy; $R_4$ is hydrogen, substituted or unsubstituted alkyl, or halogen; $R_7$ is hydrogen, substituted or unsubstituted alkyl, or hydroxy; $R_{11}$ is hydroxyl, $OSO_3H$, $OSO_3^-$, $OCOCH_3$, $OPO_3H$, $OPO_3^{2-}$, or hydrogen; and $R_{12}$ is hydroxyl, $OSO_3H$, $OSO_3^-$, $OCOCH_3$, $OPO_3H$, $OPO_3^{2-}$, or hydrogen, or taken together $R_{11}$ and $R_{12}$ form a carbonyl, provided that $R_4$ is not hydrogen, unless $R_7$ is OH.

In one aspect, the invention includes a compound having the formula E:

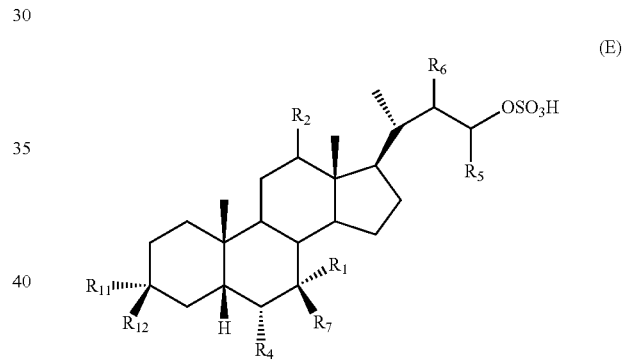

(E)

or a salt, solvate, or hydrate conjugate thereof, wherein: $R_1$ is hydrogen, hydroxy, substituted or unsubstituted alkyl, or halogen; $R_2$ is hydrogen or α-hydroxyl; $R_4$ is hydrogen, substituted or unsubstituted alkyl, or halogen; $R_5$ is hydrogen, unsubstituted alkyl, or aryl;

$R_6$ is hydrogen, unsubstituted or substituted alkyl, or $R_5$ and $R_6$ taken together with the carbons to which they are attached form a ring of size 3, 4, 5, or 6 atoms; $R_7$ is hydrogen, substituted or unsubstituted alkyl, or hydroxy; $R_{11}$ is hydroxyl, $OSO_3H$, $OSO_3^-$, $OCOCH_3$, $OPO_3H$, $OPO_3^{2-}$, or hydrogen; and $R_{12}$ is hydroxyl, $OSO_3H$, $OSO_3^-$, $OCOCH_3$, $OPO_3H$, $OPO_3^{2-}$, or hydrogen, or taken together $R_{11}$ and $R_{12}$ form a carbonyl, provided that at least one of $R_5$ or $R_6$ is not hydrogen.

In one aspect, the invention includes a compound or a salt, solvate, or hydrate thereof, wherein $R_1$ is OH. In one aspect, the invention includes a compound or a salt, solvate, or hydrate thereof, wherein $R_7$ is H. In one aspect, the invention includes a compound or a salt, solvate, or hydrate thereof, wherein $R_2$ is H. In one aspect, the invention includes a compound or a salt, solvate, or hydrate thereof, wherein $R_4$ is unsubstituted alkyl.

In one aspect, the invention includes a compound selected from

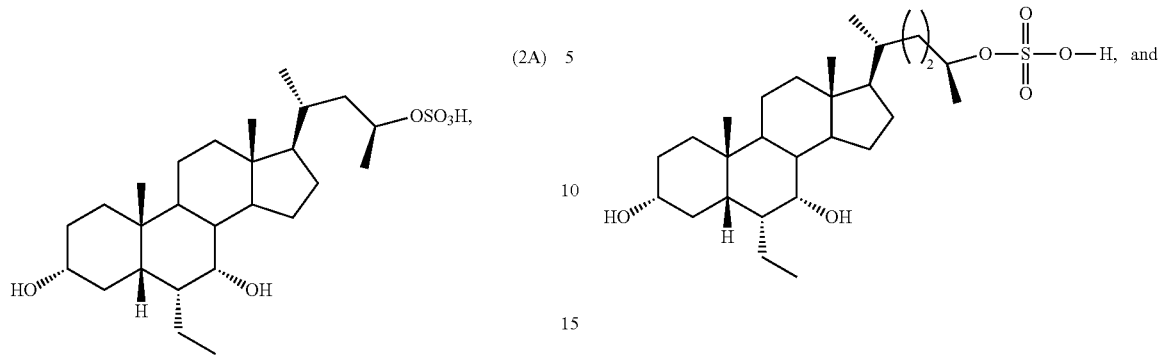

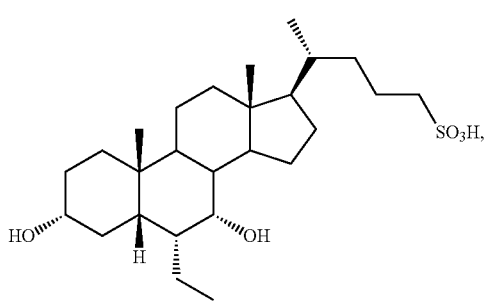

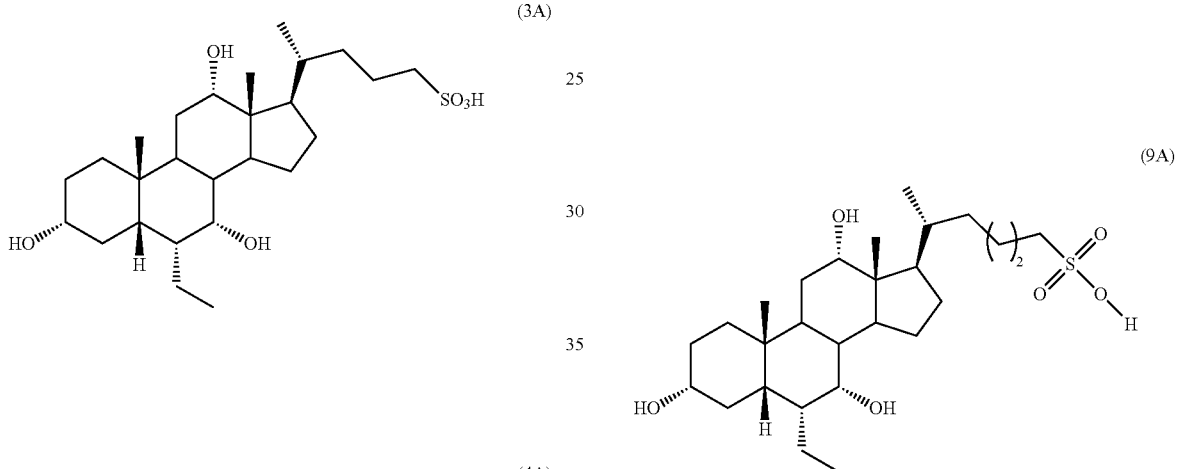

or a salt, solvate, or hydrate thereof.

In one aspect, the invention includes a compound that is a pharmaceutically acceptable salt. In one aspect, the invention includes a pharmaceutical composition comprising a compound or a salt, solvate, or hydrate thereof and at least one pharmaceutically acceptable excipient.

In another aspect, the invention includes use of a compound having the formula A or a salt, solvate, or hydrate thereof, or a pharmaceutical composition comprising a compound having the formula A or a salt, solvate, or hydrate thereof:

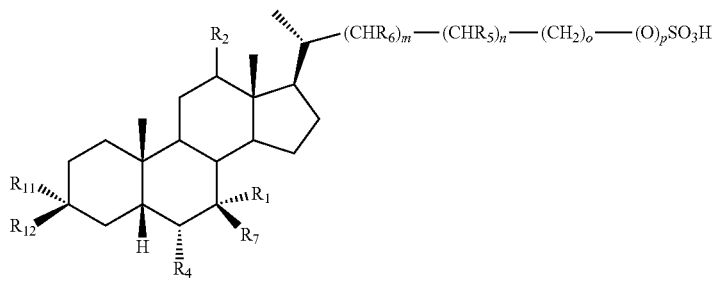

wherein:
$R_1$ is hydrogen, hydroxy, substituted or unsubstituted alkyl, or halogen; $R_2$ is hydrogen or α-hydroxy; $R_4$ is hydrogen, substituted or unsubstituted alkyl, or halogen; $R_5$ is hydrogen, unsubstituted alkyl, or aryl; $R_6$ is hydrogen, unsubstituted or substituted alkyl, or $R_5$ and $R_6$ taken together with the carbons to which they are attached form a ring of size 3, 4, 5, or 6 atoms; $R_7$ is hydrogen, substituted or unsubstituted alkyl, or hydroxy; $R_{11}$ is hydroxyl, $OSO_3H$, $OSO_3^-$, $OCOCH_3$, $OPO_3H$, $OPO_3^{2-}$ or hydrogen;
$R_{12}$ is hydroxyl, $OSO_3H$, $OSO_3^-$, $OCOCH_3$, $OPO_3H$, $OPO_3^{2-}$, or hydrogen, or taken together $R_{11}$ and $R_{12}$ form a carbonyl;
m is 0, 1, or 2; n is 0 or 1; o is 0 or 1; and p is 0 or 1, in the manufacture of a medicament for a treating or preventing a disease in a subject that involves modulation of the TGR5 receptor.

In one aspect, the invention includes the use, wherein the disease is selected from metabolic disease, inflammatory disease, liver disease, autoimmune disease, cardiac disease, kidney disease, cancer, and gastrointestinal disease. In one aspect, the invention includes the use, wherein the disease is selected from inflammatory disease and cancer. In one aspect, the invention includes the use, wherein the compound or pharmaceutical composition is administered to the subject orally, parentally, intravenously, or topically. In one aspect, the invention includes the use, wherein the subject is a human.

The above description sets forth rather broadly the more important features of the present invention in order that the detailed description thereof that follows may be understood, and in order that the present contributions to the art may be better appreciated. Other objects and features of the present invention will become apparent from the following detailed description considered in conjunction with the examples.

BRIEF DESCRIPTION OF THE FIGURES

FIG. 7 is a zoom display of FIG. 6.

FIG. 10A shows glycemia 3 weeks after treatment. FIG. 10B shows fructosamines 3 weeks after treatment. FIG. 10C shows the results of a glucose tolerance test 9 weeks after treatment.

DESCRIPTION OF THE INVENTION

Figure 1:
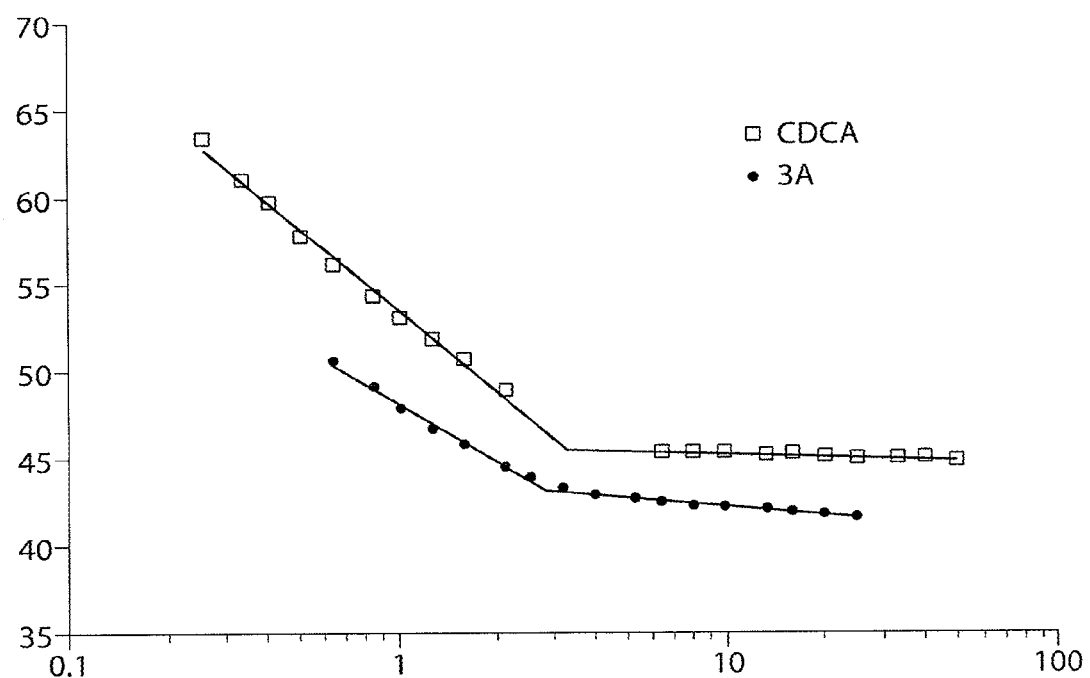
FIG. 1 is a graph that depicts the surface tension plotted against the logarithm of the concentration of 3A (mM) in NaCl 0.15M.

The details of one or more embodiments of the invention are set forth in the accompanying description below. Although any methods and materials similar or equivalent to those described herein can be used in the practice or testing of the present invention, the methods and materials are now described. Other features, objects, and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present specification will control.

In one aspect, the invention provides a compound having the formula A:

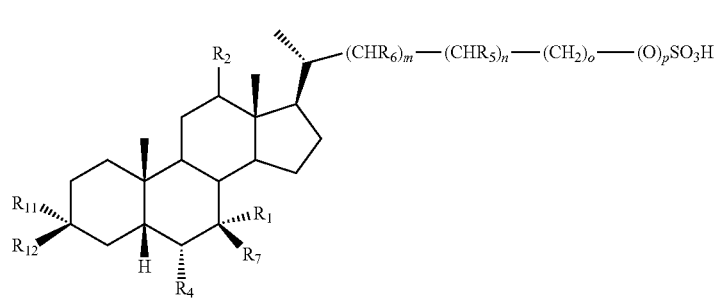

(A)

or a salt, solvate, or hydrate, wherein $R_1$ is hydrogen, hydroxy, substituted or unsubstituted alkyl, or halogen; $R_2$ is hydrogen or α-hydroxy; $R_4$ is hydrogen, substituted or unsubstituted alkyl, or halogen; $R_5$ is hydrogen, unsubstituted alkyl, or aryl; $R_6$ is hydrogen, unsubstituted or substituted alkyl, or $R_5$ and $R_6$ taken together with the carbons to which they are attached form a ring of size 3, 4, 5, or 6 atoms; $R_7$ is hydrogen, substituted or unsubstituted alkyl, or hydroxy; $R_{11}$ is hydroxyl, $OSO_3H$, $OSO_3^-$, $OCOCH_3$, $OPO_3H$, $OPO_3^{2-}$ or hydrogen; $R_{12}$ is hydroxyl, $OSO_3H$, $OSO_3^-$, $OCOCH_3$, $OPO_3H$, $OPO_3^{2-}$ or hydrogen, or taken together $R_{11}$ and $R_{12}$ form a carbonyl; m is 0, 1 or 2; n is 0 or 1; o is 0 or 1; and p is 0 or 1.

In one aspect, the invention provides that when m+n+o=3 or 4, p is zero, and $R_5$ is $R_6$ hydrogen, then $R_4$ is not hydrogen, unless $R_7$ is OH. In another aspect, the invention provides that when m+n+o=3 or 4, p is zero, and $R_5$ is not unsubstituted alkyl or aryl, then $R_4$ is not hydrogen, unless $R_7$ is OH.

In one aspect, the invention provides that when m+n+o=3, p is 1, and $R_5$ and $R_6$ are each hydrogen, then at least one of $R_2$ and $R_4$ is not hydrogen.

In one aspect, the invention provides that when m+n+o=2, and at least one of $R_5$ and $R_6$ is not hydrogen.

In one aspect, the invention does not include compounds A, B, and C:

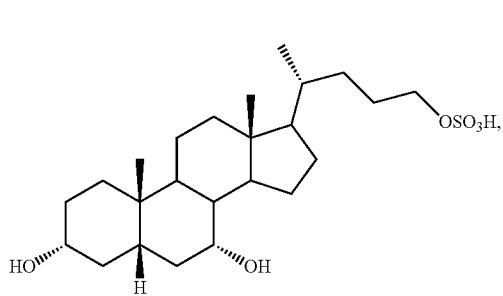

(A)

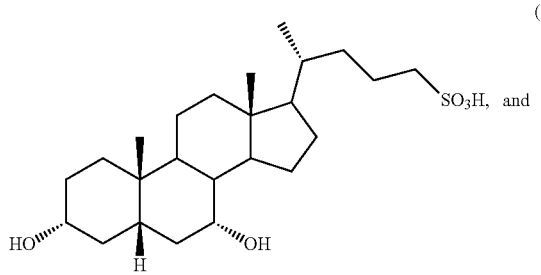

(B)

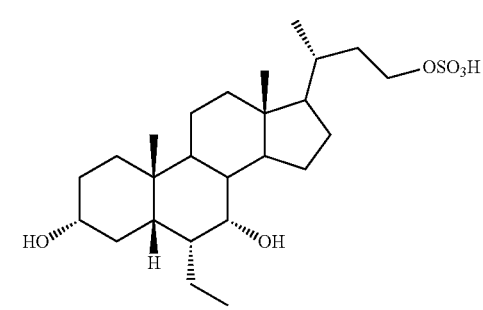

(C)

or a salt, solvate, or hydrate thereof. In another aspect, the invention does not include compound 6A or a salt, solvate, or hydrate thereof. In another aspect, the invention does not include compound 7A or a salt, solvate, or hydrate thereof.

In one aspect, the invention provides a compound having the formula B:

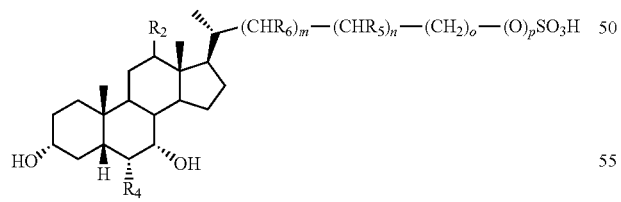

(B)

or a salt, solvate, or hydrate thereof, wherein $R_2$, $R_4$, $R_5$, and $R_6$, m, n, o, and p are as described above. In one aspect, the invention provides that when m+n+o=3 or 4, p is zero, $R_5$ is hydrogen, then $R_4$ is not hydrogen. In one aspect, the invention provides that when m+n+o=3, p is 1, and $R_5$ and $R_6$ are each hydrogen, then at least one of $R_2$ and $R_4$ is not hydrogen. In another aspect, the invention provides that when m+n+o=2, then at least one of $R_5$ and $R_6$ is not hydrogen.

In one aspect, the invention provides a compound having the formula C:

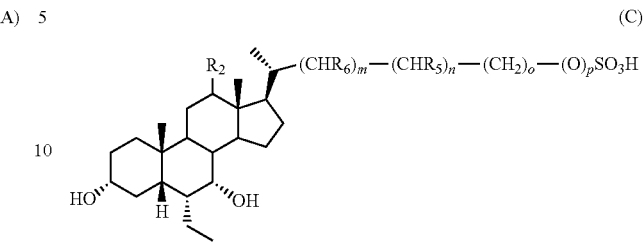

(C)

or a salt, solvate, or hydrate thereof, wherein $R_2$, $R_5$, $R_6$, m, n, o, and p are as described above. In one aspect, when m+n+o=2, then at least one of $R_5$ and $R_6$ is not hydrogen.

In one aspect, the invention provides a compound having the formula D:

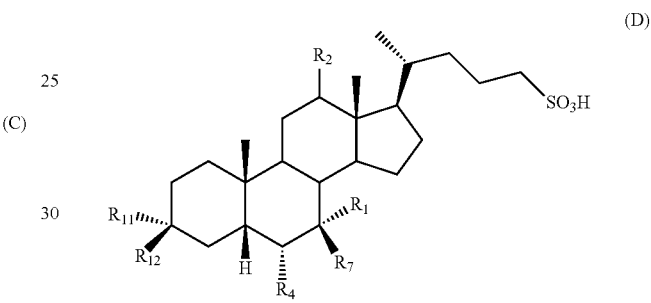

(D)

or a salt, solvate, or hydrate thereof, wherein $R_1$, $R_2$, $R_4$, $R_7$, $R_{11}$, and $R_{12}$ are as described above. In one aspect, $R_4$ is not hydrogen.

In one aspect, the invention provides a compound having the formula E:

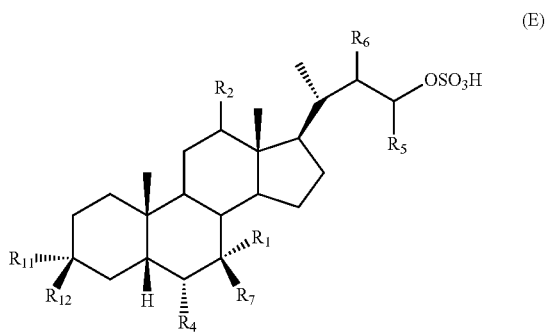

(E)

or a salt, solvate, or hydrate thereof, wherein: $R_1$ is hydrogen, hydroxy, substituted or unsubstituted alkyl, or halogen; $R_2$ is hydrogen or α-hydroxyl; $R_4$ is hydrogen, substituted or unsubstituted alkyl, or halogen; $R_5$ is hydrogen, unsubstituted alkyl, or aryl; $R_6$ is hydrogen, unsubstituted or substituted alkyl, or $R_5$ and $R_6$ taken together with the carbons to which they are attached form a ring of size 3, 4, 5, or 6 atoms; $R_7$ is hydrogen, substituted or unsubstituted alkyl, or hydroxy; $R_{11}$ is hydroxyl, $OSO_3H$, $OSO_3^-$, $OCOCH_3$, $OPO_3H$, $OPO_3^{2-}$ or hydrogen; and $R_{12}$ is hydroxyl, $OSO_3H$, $OSO_3^-$, $OCOCH_3$, $OPO_3H$, $OPO_3^{2-}$ or hydrogen, or taken together $R_{11}$ and $R_{12}$ form a carbonyl. In one aspect, the invention provides that at least one of $R_5$ or $R_6$ is not hydrogen.

In one aspect, the invention provides a compound having the formula F:

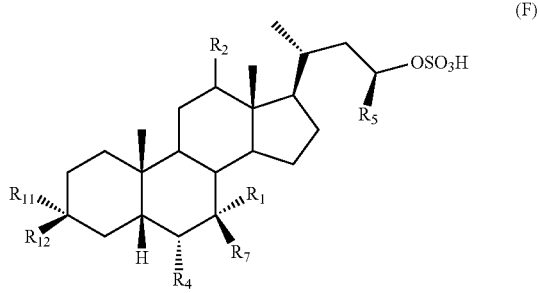

(F)

or a salt, solvate, or hydrate thereof, wherein $R_5$ is unsubstituted or substituted alkyl or aryl; and
$R_1$, $R_2$, $R_4$, $R_7$, $R_{11}$, and $R_{12}$ are as described above.

In one aspect, the invention provides a compound having the formula G:

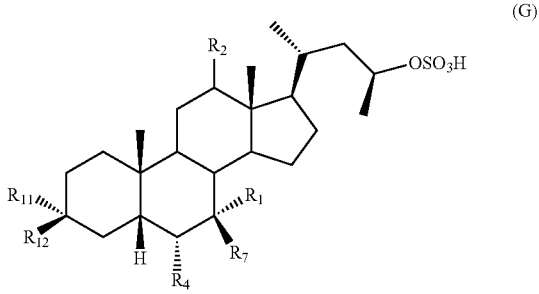

(G)

or a salt, solvate, or hydrate thereof, wherein $R_1$, $R_2$, $R_4$, $R_7$, $R_{11}$, and $R_{12}$ are as described above.

In one aspect, the invention provides a compound having the formula H:

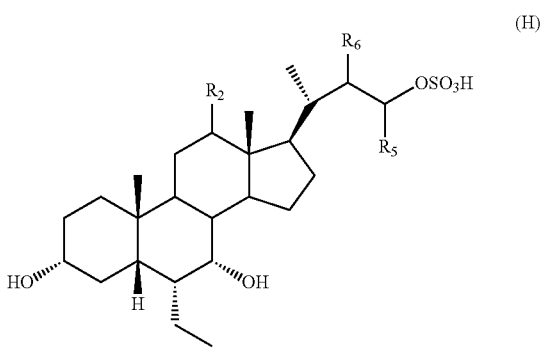

(H)

or a salt, solvate, or hydrate thereof, wherein $R_2$, $R_5$ and $R_6$ are as described above.

In one aspect, the invention provides a compound or a salt, solvate, or hydrate thereof, wherein $R_1$ is OH.

In one aspect, the invention provides a compound or a salt, solvate, or hydrate thereof, wherein $R_7$ is H.

In one aspect, the invention provides a compound or a salt, solvate, or hydrate thereof, wherein $R_1$ is OH and $R_7$ is H.

In one aspect, the invention provides a compound or a salt, solvate, or hydrate thereof, wherein $R_2$ is H. In one aspect, the invention provides a or a salt, solvate, or hydrate thereof, wherein $R_2$ is alpha-OH. In one aspect, the invention provides a salt, solvate, or hydrate thereof, wherein $R_2$ is beta-OH.

In one aspect, the invention provides a compound or a salt, solvate, or hydrate thereof, wherein $R_4$ is unsubstituted alkyl. In one aspect, the invention provides a compound or a salt, solvate, or hydrate thereof, wherein $R_4$ is ethyl. In one aspect, the invention provides a compound or a salt, solvate, or hydrate thereof, wherein $R_4$ is methyl.

In one aspect, the invention provides a compound or a salt, solvate, or hydrate thereof, wherein $R_5$ is not hydrogen. In one aspect, the invention provides a compound or a salt, solvate, or hydrate thereof, wherein $R_5$ is unsubstituted alkyl. In one aspect, the invention provides a compound or a salt, solvate, or hydrate thereof, wherein $R_5$ is methyl.

In one aspect, the invention provides a compound or a salt, solvate, or hydrate thereof, wherein $R_6$ is hydrogen.

In one aspect, the invention provides a compound of salt, solvate, or hydrate thereof, wherein $R_5$ and $R_6$ are both hydrogen.

In one aspect, the invention provides a compound or a salt, solvate, or hydrate thereof, wherein $R_{11}$ is hydroxyl. In one aspect, the invention provides a compound or a salt, solvate, or hydrate thereof, wherein $R_{12}$ is hydrogen. In one aspect, the invention provides a compound or a salt, solvate, or hydrate thereof, wherein $R_{11}$ is hydroxyl and $R_{12}$ is hydrogen.

In one aspect, the invention provides a compound or a salt, solvate, or hydrate thereof, wherein m is 1. In one aspect, the invention provides a compound or a salt, solvate, or hydrate thereof, wherein m is 2. In one aspect, the invention provides a compound or a salt, solvate, or hydrate thereof, wherein n is 1.

In one aspect, the invention provides a compound or a salt, solvate, or hydrate thereof, wherein p is 0. In one aspect, the invention provides a compound or a salt, solvate, or hydrate thereof, wherein o is 1.

In one aspect, the invention provides a compound or a salt, solvate, or hydrate thereof, wherein p is 1. In one aspect, the invention provides a compound or a salt, solvate, or hydrate thereof, wherein p is 0.

In one aspect, the invention provides a compound or a salt, solvate, or hydrate thereof, wherein $R_4$ is ethyl and p is 1. In one aspect, the invention provides a compound or a salt, solvate, or hydrate thereof, wherein $R_4$ is ethyl and the compound contains a sulfonate moiety. In one aspect, the invention provides a compound or a salt, solvate, or hydrate thereof, wherein $R_4$ is hydrogen or substituted or unsubstituted alkyl and p is 0.

In one aspect, the invention provides a compound selected from
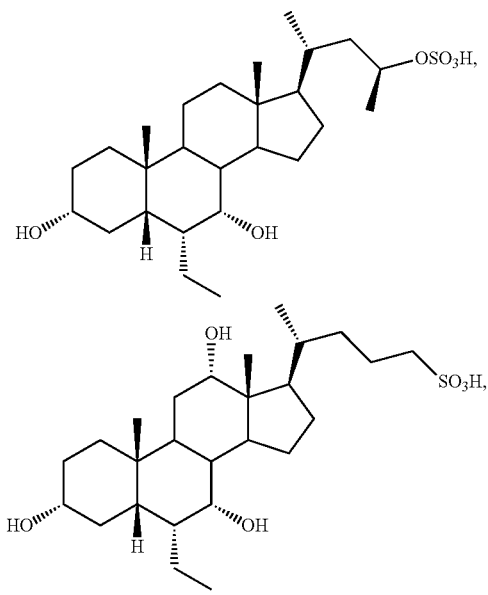
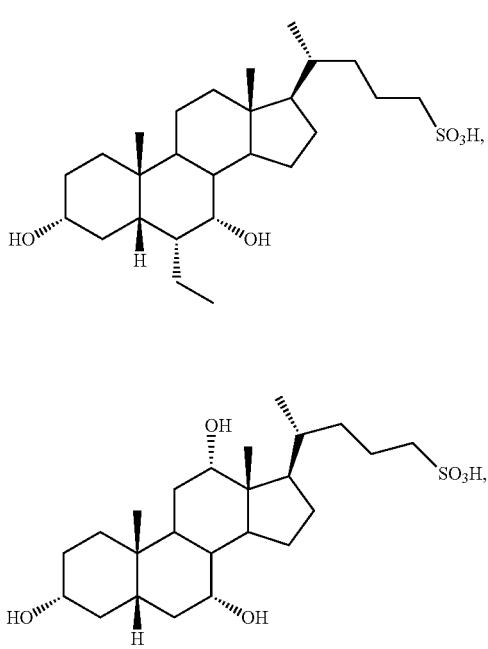
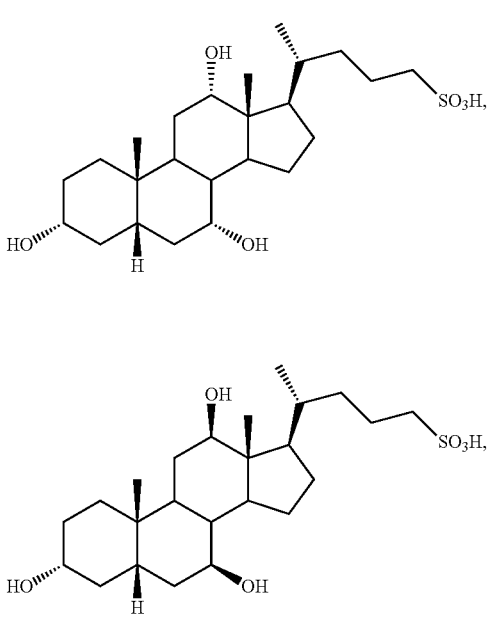
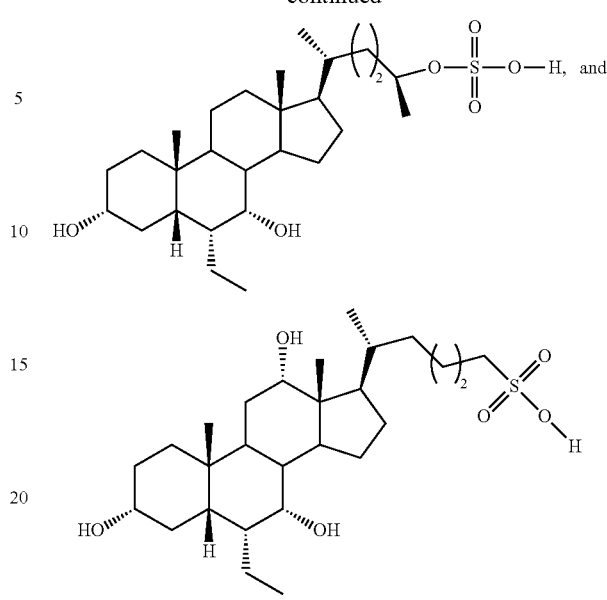
or a salt, solvate, or hydrate thereof.
In one aspect, the invention provides a compound, wherein the compound is a pharmaceutically acceptable salt.
In one aspect, the invention provides a pharmaceutically acceptable salt selected from
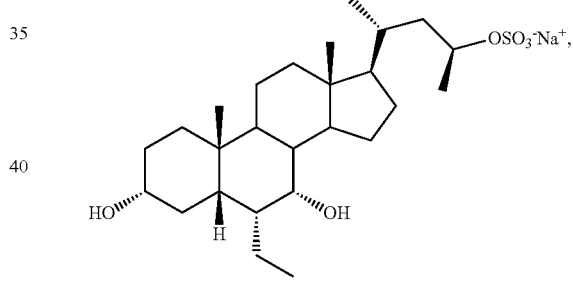
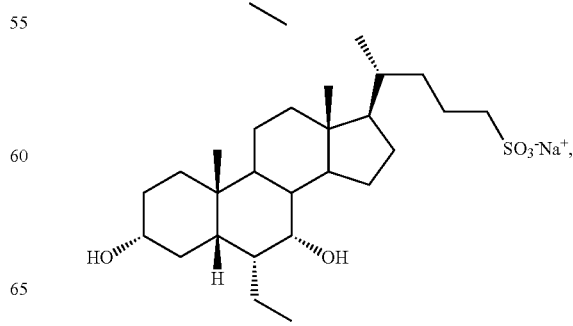

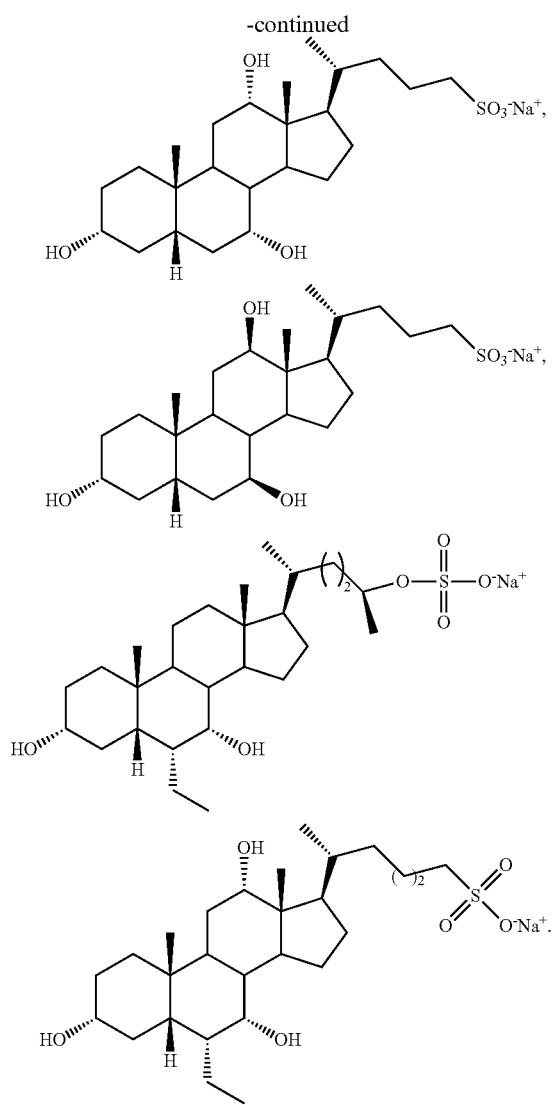

In one aspect, the invention provides a pharmaceutical composition comprising a compound and at least one pharmaceutically acceptable excipient.

In one aspect, the invention provides the use of a compound or a pharmaceutical composition of the invention, in the manufacture of a medicament for treating or preventing a disease in a subject. In another aspect, the invention provides a method of treating or preventing disease in a subject by administering a compound or a pharmaceutical composition of the invention. In one aspect, the invention provides a therapeutically effective amount of a compound or pharmaceutical composition of the invention is administered to the subject. In one aspect, the invention provides a prophylactically effective amount of a compound or pharmaceutical composition of the invention is administered.

In one aspect, the invention provides the use of the compound or pharmaceutical composition of the invention, in the manufacture of a medicament for a treating or preventing a disease in a subject that involves modulation of the TGR5 receptor. The invention includes a method of treating or preventing a disease that involves modulation of the TGR5 receptor in a subject by administering a compound or pharmaceutical composition of the invention.

In one aspect, the invention provides the use, wherein the disease is selected from metabolic disease, inflammatory disease, liver disease, autoimmune disease, cardiac disease, kidney disease, cancer, and gastrointestinal disease using a compound having the formula A, B, C, D, E, F, or G. The invention includes a method of treating or preventing a disease selected from metabolic disease, inflammatory disease, liver disease, autoimmune disease, cardiac disease, kidney disease, cancer, and gastrointestinal disease using a compound of formula A, B, C, D, E, F, or G. The invention includes a method of treating or preventing inflammatory disease or cancer using a compound of formula A, B, C, D, E, F, or G.

In one aspect, the invention provides for the use, wherein the disease is a metabolic disease selected from obesity, diabetes, metabolic syndrome, insulin resistance, hypertension, and dyslipidemia. The invention includes a method of treating or preventing a metabolic disease selected from obesity, diabetes, metabolic syndrome, insulin resistance, hypertension, and dyslipidemia.

In one aspect, the invention provides for the use, wherein the disease is an inflammatory disease selected from allergy, osteoarthritis, appendicitis, bronchial asthma, pancreatitis, allergic rash, and psoriasis. The invention includes a method of treating or preventing an inflammatory disease selected from allergy, osteoarthritis, appendicitis, bronchial asthma, pancreatitis, allergic rash, and psoriasis.

In one aspect, the invention provides for the use, wherein the disease is an autoimmune disease selected from rheumatoid arthritis, multiple sclerosis, and type I diabetes. The invention includes a method of treating or preventing an autoimmune disease selected from rheumatoid arthritis, multiple sclerosis, and type I diabetes.

In one aspect, the invention provides for the use, wherein the disease is a gastrointestinal disease selected from inflammatory bowel disease (Crohn's disease, ulcerative colitis), short bowel syndrome (post-radiation colitis), microscopic colitis, irritable bowel syndrome (malabsorption), and bacterial overgrowth. The invention includes a method of treating or preventing a gastrointestinal disease selected from inflammatory bowel disease (Crohn's disease, ulcerative colitis), short bowel syndrome (post-radiation colitis), microscopic colitis, irritable bowel syndrome (malabsorption), and bacterial overgrowth.

In one aspect, the invention provides for the use, wherein the disease is kidney disease selected from diabetic nephropathy, chronic renal failure, hypertensive nephrosclerosis, chronic glomerulonephritis, chronic transplant glomerulopathy, chronic interstitial nephritis, and polysystic kidney disease. The invention includes a method of treating or preventing kidney disease selected from diabetic nephropathy, chronic renal failure, hypertensive nephrosclerosis, chronic glomerulonephritis, chronic transplant glomerulopathy, chronic interstitial nephritis, and polysystic kidney disease.

In one aspect, the invention provides for the use, wherein the disease is cancer selected from colorectal cancer, liver cancer, heptacellular carcinoma, cholangio carcinoma, renal cancer, gastric cancer, pancreatic cancer, prostate cancer, and insulanoma. The invention includes a method of treating or preventing cancer selected from colorectal cancer, liver cancer, heptacellular carcinoma, cholangio carcinoma, renal cancer, gastric cancer, pancreatic cancer, prostate cancer, and insulanoma.

In one aspect, the invention provides for the use, wherein the disease is a liver disease selected from nonalcoholic steatohepatitis, nonalcoholic fatty liver disease, chronic viral hepatitis, alcoholic liver disease, drug induced hepatitis, hemochromatosis, primary biliary cirrhosis, primary sclerosing cholangitis, portal hypertension, bile desaturation, Gaucher's disease, Wilson's disease, α1-antitrypsin deficiency, total parenteral nutrition (TPN), cholelithiasis, TPN-associated cholestasis and sepsis. The invention includes a method of treating or preventing a liver disease selected from nonalcoholic steatohepatitis, nonalcoholic fatty liver disease, chronic viral hepatitis, alcoholic liver disease, drug induced hepatitis, hemochromatosis, primary biliary cirrhosis, primary sclerosing cholangitis, portal hypertension, bile desaturation, Gaucher's disease, Wilson's disease, α1-antitrypsin deficiency, total parenteral nutrition (TPN), cholelithiasis, TPN-associated cholestasis and sepsis.

In one aspect, the invention provides for the use, wherein the cardiac disease is selected from congestive heart failure, myocardial infarction, atherosclerosis, angina pectoris, arteriosclerosis and cerebrovascular disease (hemorrhage, stroke, cerebrovascular infarction). The invention includes a method of treating or preventing a cardiac disease selected from congestive heart failure, myocardial infarction, atherosclerosis, angina pectoris, arteriosclerosis and cerebrovascular disease (hemorrhage, stroke, cerebrovascular infarction).

In one aspect, the disease involves modulation of the TGR5 receptor. In one aspect, the compound is a TGR5 agonist. In one aspect, the compound is a selective TGR5 agonist over FXR activator. In one aspect, the compound is a partial modulator of FXR. In one aspect, the compound is a partial FXR agonist.

In one aspect, the compound or pharmaceutical composition of the invention is administered to the subject orally, parentally, intravenously, or topically. In one aspect, the subject is a human.

DEFINITIONS

For convenience, certain terms used in the specification, examples and appended claims are collected here.

The term "treating", as used herein, means relieving, lessening, reducing, eliminating, modulating, or ameliorating, i.e. causing regression of the disease state or condition. Treating can also include inhibiting, i.e. arresting the development, of a existing disease state or condition, and relieving or ameliorating, i.e. causing regression of an existing disease state or condition, for example when the disease state or condition may already be present.

The term "preventing", as used herein means, to completely or almost completely stop a disease state or condition, from occurring in a patient or subject, especially when the patient or subject is predisposed to such or at risk of contracting a disease state or condition.

"Alkyl" includes saturated aliphatic groups, including straight-chain alkyl groups (e.g., methyl, ethyl, propyl, butyl, pentyl, hexyl, heptyl, octyl, nonyl, decyl), branched-chain alkyl groups (e.g., isopropyl, tert-butyl, isobutyl). In certain embodiments, a straight chain or branched chain alkyl has six or fewer carbon atoms in its backbone (e.g., $C_1$-$C_6$ for straight chain, $C_3$-$C_6$ for branched chain). In some examples, a straight chain or branched chain alkyl has four or fewer carbon atoms in its backbone.

As used herein, "cycloalkyl" is intended to include saturated ring groups, such as cyclopropyl, cyclobutyl, or cyclopentyl. C3-8 cycloalkyl is intended to include C3, C4, C5, C6, C7, and C8 cycloalkyl groups.

The term "substituted alkyl" refers to an alkyl moieties having a substituent replace one or more hydrogen atoms on at least one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aryl" includes groups with aromaticity, including 5- and 6-membered "unconjugated", or single-ring, aromatic groups that may include from zero to four heteroatoms, as well as "conjugated", or multicyclic, systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxarole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at least one ring position with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

Unless the number of carbons is otherwise specified, "lower alkyl" includes an alkyl group, as defined above, but having from one to ten, for example, from one to six, carbon atoms in its backbone structure.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "hydroxy" or "hydroxyl" includes groups with an —OH or —O⁻.

The term "halogen" includes fluorine, bromine, chlorine, iodine, etc. The term "perhalogenated" generally refers to a moiety wherein all hydrogens are replaced by halogen atoms.

An "anionic group," as used herein, refers to a group that is negatively charged at physiological pH. Anionic groups include carboxylate, sulfate, sulfonate, sulfinate, sulfamate, tetrazolyl, phosphate, phosphonate, phosphinate, or phosphorothioate or functional equivalents thereof. "Functional equivalents" of anionic groups are intended to include bioisosteres, e.g., bioisosteres of a carboxylate group. Bioisosteres encompass both classical bioisosteric equivalents and non-classical bioisosteric equivalents. Classical and non-classical bioisosteres are known in the art (see, e.g., Silverman, R. B. The Organic Chemistry of Drug Design and Drug Action, Academic Press, Inc.: San Diego, Calif., 1992, pp. 19-23). Another anionic group is a carboxylate.

The term "unstable functionality" refers to a substitution pattern that contains a labile linkage, e.g., a functionality or bond that is susceptible to hydrolysis or cleavage under physiological conditions (e.g., aqueous solutions in the neutral pH range). Examples of unstable functionalities include acetals and ketals.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

It will be noted that the structure of some of the compounds of the invention include asymmetric carbon atoms. It is to be understood accordingly that the isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Enantiomers (R- and S-configurations) are named according to the system developed by R. S. Cahn, C. Ingold, and V. Prelog.

Further, the structures and other compounds discussed in this application include all atropic isomers thereof. Atropic isomers are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Stable compound" and "stable structure" are meant to indicate a compound that is sufficiently robust to survive isolation to a useful degree of purity from a reaction mixture, and formulation into an efficacious therapeutic agent.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

As defined herein, the term "derivative", e.g., in the term "bile acid derivatives", refers to compounds that have a common core 4-membered ring structure, and are substituted with various groups as described herein.

The chemical compounds described herein can have asymmetric centers. Compounds of the present invention containing an asymmetrically substituted atom can be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and can be isolated as a mixture of isomers or as separated isomeric forms. All chiral, diastereomeric, racemic, and geometric isomeric forms of a structure are intended, unless the specific stereochemistry or isomeric form is specifically indicated. All processes used to prepare compounds of the present invention and intermediates made therein are, where appropriate, considered to be part of the present invention. All tautomers of shown or described compounds are also, where appropriate, considered to be part of the present invention.

The term "bioisostere" refers to a compound resulting from the exchange of an atom or of a group of atoms with another, broadly similar, atom or group of atoms. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

The phrase "pharmaceutically acceptable" is art-recognized. In certain aspects, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water, (17) isotonic saline; (18) Ringer's solution; (19) ethyl alcohol; (20) phosphate buffer solutions; and (21) other non-toxic compatible substances employed in pharmaceutical formulations.

"Combination therapy" (or "co-therapy") includes the administration of a compound of the invention and at least a second agent as part of a specific treatment regimen intended to provide the beneficial effect from the co-action of these therapeutic agents (i.e., the compound of the invention and at least a second agent). The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or mechanical treatments). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The terms "parenteral administration" and "administered parenterally" as used herein refer to modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

A "therapeutically effective amount" of a compound of the invention, or a combination of compounds is an amount (quantity or concentration) of compound or compounds. In one embodiment, when a therapeutically effective amount of a compound is administered to a subject in need of treatment symptoms arising from the disease are ameliorated immediately or after administration of the compound one or more times. The amount of the compound to be administered to a subject will depend on the particular disorder, the mode of administration, co-administered compounds, if any, and the characteristics of the subject, such as general health, other diseases, age, sex, genotype, body weight and tolerance to drugs. The skilled artisan will be able to determine appropriate dosages depending on these and other factors.

The term "prophylactically effective amount" means an amount (quantity or concentration) of a compound of the present invention, or a combination of compounds, that is administered to prevent or reduce the risk of a disease—in other words, an amount needed to provide a preventative or prophylactic effect. The amount of the present compound to be administered to a subject will depend on the particular disorder, the mode of administration, co-administered compounds, if any, and the characteristics of the subject, such as general health, other diseases, age, sex, genotype, body weight and tolerance to drugs.

The term "reducing the risk of", as used herein, means to lower the likelihood or probability of a disease from occurring in a patient, especially when the patient or subject is predisposed to such occurrence.

A "salt" of a compound of the invention is a product of the compound that contains an ionic bond and its typically produced by reacting the compound with either an acid or a base.

A "pharmaceutically acceptable salt" is a salt suitable for administering to a subject.

As used herein, a "pharmaceutically acceptable salt" refer to a derivative of a disclosed compound wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, and toluene sulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 18th ed., Mack Publishing Company, Easton, Pa. USA, p. 1445 (1990).

A "pharmaceutical composition" is a formulation containing a compound of the invention in a form suitable for administration to a subject. In another embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of a compound of the invention or salts thereof) in a unit dose of pharmaceutical composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, and the like. Dosage forms for the topical or transdermal administration of a compound of this invention include powders, sprays, ointments, pastes, creams, lotions, gels, solutions, patches and inhalants. In another embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). Typically, the subject is human.

Compounds of the invention also include prodrugs or physiologically equivalent derivatives. A "prodrug" or "physiologically equivalent derivative" includes a precursor form of the drug which is metabolically converted in vivo to produce the active drug. The invention further contemplates the use of prodrugs which are converted in vivo to the TGR5 modulating compounds used in the methods of the invention (see, e.g., R. B. Silverman, 1992, "The Organic Chemistry of Drug Design and Drug Action", Academic Press, Chp. 8). Such prodrugs can be used to alter the biodistribution (e.g., to allow compounds which would not typically cross the blood-brain barrier to cross the blood-brain barrier) or the pharmacokinetics of the TGR5 modulating compound. For example, an anionic group, e.g., a carboxylate, sulfate or sulfonate, can be esterified, e.g., with an alkyl group (e.g., a methyl group) or a phenyl group, to yield an ester. When the ester is administered to a subject, the ester is cleaved, enzymatically or non-enzymatically, reductively or hydrolytically, to reveal the anionic group. Such an ester can be cyclic, e.g., a cyclic sulfate or sulfone, or two or more anionic moieties may be esterified through a linking group. An anionic group can be esterified with moieties (e.g., acyloxymethyl esters) which are cleaved to reveal an intermediate TGR5 modulating compound which subsequently decomposes to yield the active TGR5 modulating compound. In one embodiment, the prodrug is a reduced form of a carboxylate, sulfate or sulfonate, e.g., an alcohol or thiol, which is oxidized in vivo to the TGR5 modulating compound. Furthermore, an anionic moiety can be esterified to a group which is actively transported in vivo, or which is selectively taken up by target organs.

The term "TGR5 modulator" means any compound that interacts with the TGR5 receptor. The interaction is not limited to a compound acting as an antagonist, agonist, partial agonist, or inverse agonist of the TGR5 receptor. In one aspect, the compounds of the present invention act as an antagonist of the TGR5 receptor. In another aspect, the compounds of the present invention act as an agonist of the TGR5 receptor. In another aspect, the compounds of the present invention act as a partial agonist of the TGR5 receptor. In another aspect, the compounds of the present invention act as an inverse agonist of the TGR5 receptor. The profile of a ligand, traditionally, endogenous or synthetic, is characterized by its intrinsic efficacy 'e' originally described by Furchgott in 1966. It is used to express the degree to which the different ligands produce varying biological responses while occupying the same number of receptors. Generally, the term "agonist" means a compound that enhances the activity of another molecule or receptor site. An agonist, by classical definition, whether a orthosteric, allosteric, inverse or a co-agonist has a property to bind to the receptor, alter its receptor state and result in a biological action. Consequently, agonism is defined as a property of an agonist or a ligand to produce a biological action. In contrast to this, an "antagonist" is essentially an agonist with high affinity to the same receptor macromolecule, but with very less or negligible intrinsic efficacy, and thus sterically prevents the biological actions of an agonist. As a property, antagonism may be functional or physiological, where an agonist has a direct competition for the receptor site in former and opposing effects via a different receptor-messenger system in the later. More specifically, a TGR5 agonist is a receptor ligand or compound that binds to TGR5 and increases the concentration of cyclic adenosine monophosphate (cAMP) by at least 20% in cells expressing the receptor." Conversely, a TGR5 antagonist would be a compound that antagonizes or blocks the activity of an agonist, thereby effecting a reduction in the concentration of cAMP The present invention relates to compounds having TGR5 receptor modulating activity and their use to treat and prevent metabolic diseases such as metabolic, inflammatory, liver, autoimmune, cardiac, kidney, cancer and gastrointestinal disease.

Some representative compounds of the invention are shown below.

| Compound No. | Structure |
|---|---|
| 2A | 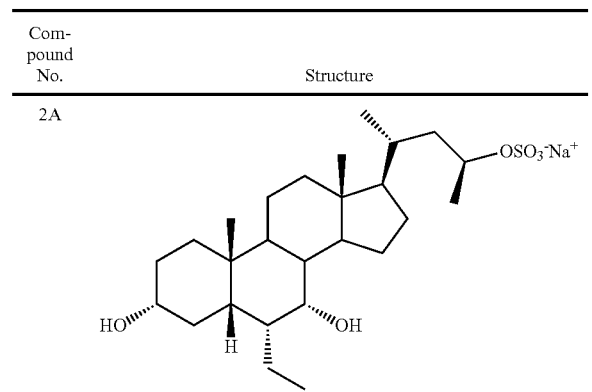 |

| Compound No. | Structure |
|---|---|
| 3A | 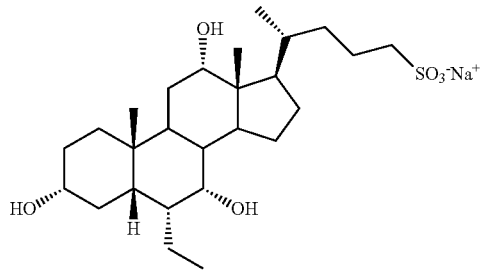 |
| 4A | 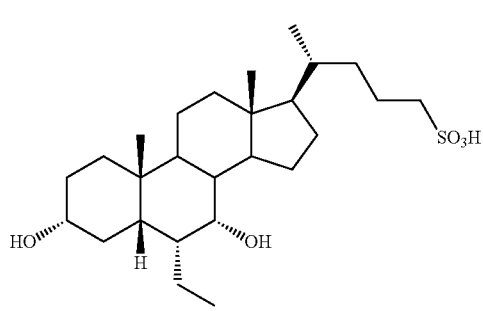 [SMILES: CC[C@H]1[C@@H](O)C2C3CC[C@H]([C@H](C)CCCS(=O)(=O)O)[C@@]3(C)CCC2[C@@]2(C)CC[C@@H](O)C[C@@H]12] |
| 6A | 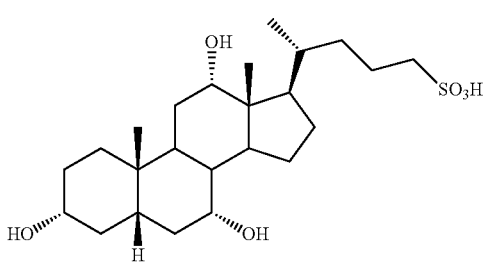 [SMILES: C[C@H](CCCS(=O)(=O)O)[C@H]1CCC2C3C(C[C@H](O)[C@@]21C)[C@@]1(C)CC[C@@H](O)C[C@H]1C[C@H]3O] |
| 7A | 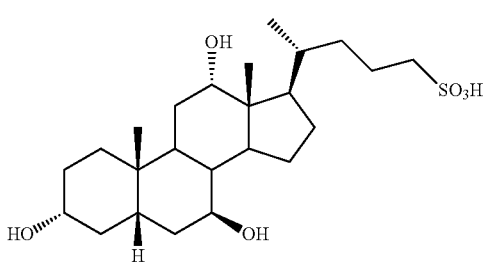 [SMILES: C[C@H](CCCS(=O)(=O)O)[C@H]1CCC2C3C(C[C@H](O)[C@@]21C)[C@@]1(C)CC[C@@H](O)C[C@H]1C[C@@H]3O] |
| 8A | 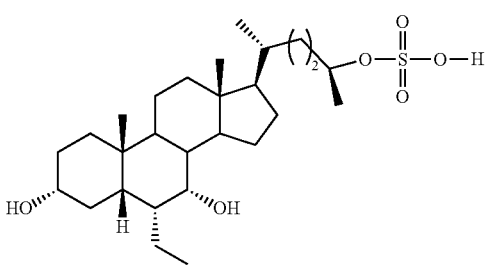 |

| Compound No. | Structure |
|---|---|
| 9A | 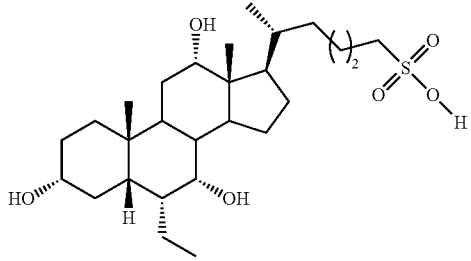 |

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

Example 1

Synthesis of TGR5 Modulators

The compounds of the invention, and related derivatives, can be synthesized by methods known to one skilled in the art.

Example 1A

Synthesis of 3α,7α,12α-trihydroxy-6α-ethyl-5β-cholan-24-sulfonate sodium salt (3A)

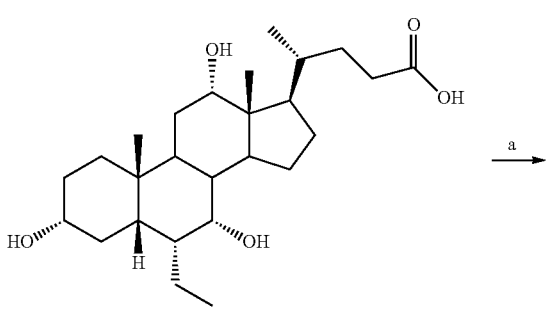

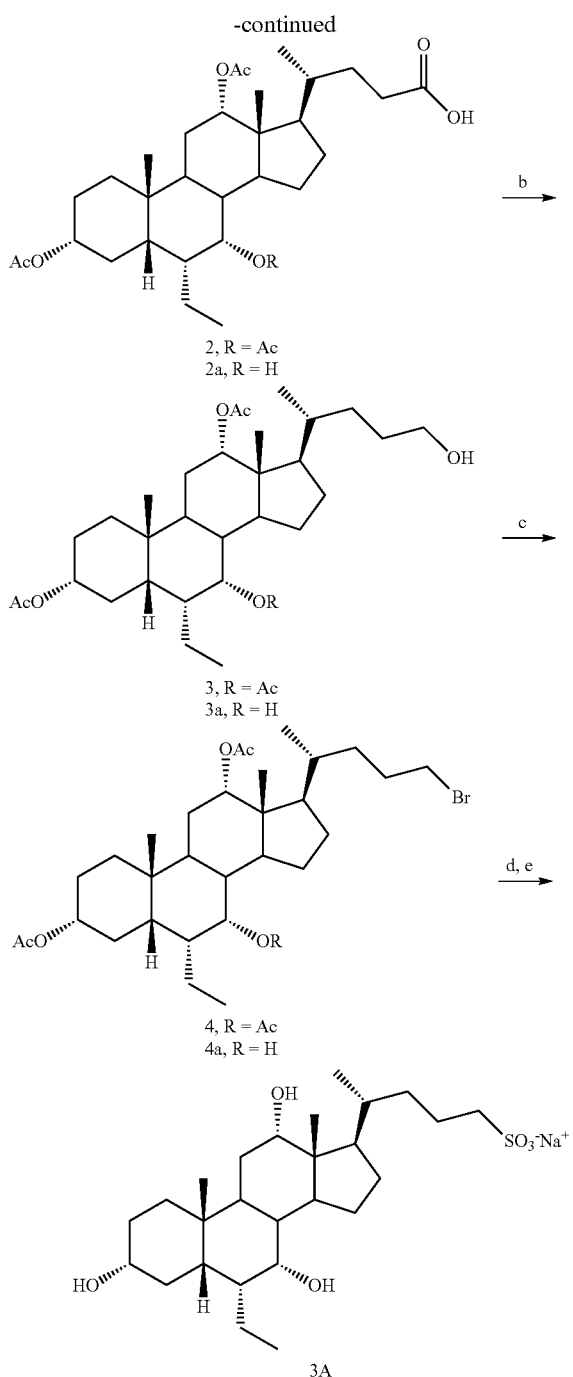

Reagent and conditions:
a) Et₃N, 4-Pyrrolidin-Pyridine, Ac₂O, CH₂Cl₂, 0° C., (2:2a = 70:30);
b) Et₃N, ClCOOEt, THF, NaBH₄, 41% from 1 (3:3a = 70:30);
c) Ph₃P, Br₂, Imidazole, CH₂Cl₂, 45% (4:4a = 70:30);
d) Na₂SO₃, EtOH;
e) NaOH 5% in H₂O, 93%. Overall yield: 17%.

3α,7α,12α-triacetoxy-6α-ethyl-5β-cholan-24-oic acid (2)

To a cooled (0° C.) and stirred suspension of 1 (250 mg, 0.572 mmol) in distilled CH₂Cl₂ (5 ml) in presence of 4-Pyrrolidin Piridine (9 mg, 0.057 mmol), distilled Et3N (0.78 ml, 5.430 mmol) was added was added. Subsequently acetic anhydride (0.49 ml, 5.140 mmol) was added dropwise under nitrogen atmosphere. After 20' the solution was warmed to room temperature and stirred overnight. The mixture was concentrated under reduced pressure, and the resulting residue was acidified with HCl 3N and extracted with AcOEt (3×15 ml). The organic layer was washed with brine (15 ml), dried over anhydrous Na₂SO₄, and concentrated under reduced pressure, to give 290 mg of mixture of 2 (70%) and 3α,7α-triacetoxy-7α-hydroxy-6α-ethyl-5β-cholan-24-oic acid (2a, 30%) as resulted from ¹H-NMR analysis. The mixture was used for the following step without further purification.

¹H-NMR (200 MHz, CDCl₃) δ: 0.69 (3H, s, 18-CH₃ of 2), 0.75 (3H, s, 18-CH₃ of 2a), 0.80-0.88 (m, 9H, m, 19-CH₃+21-CH₃+CH₂CH₃ of 2 and 2a), 2.05 (9H, m, 3×CH₃COO— of 2 and of 2a), 3.67 (1H, m, 7-CH—OH of 2a), 4.48 (1H, nm, 3-CHOAc of 2 and of 2a), 5.01 (1H, m, 12-CHOAc of 2 and of 2a), 5.12 (1H, m, 7-CHOAc of 2).

3α,7α,12α-triacetoxy-6α-ethyl-24-hydroxy-5β-cholane (3)

To a solution of 2 (290 mg, crude of previous step) in distilled THF (35 ml) under N₂ atmosphere, distilled Et3N (0.75 ml, 5.148 mmol) and then ethylchloroformiate (0.44 ml, 4.576 mmol) were added (NOTE: formation of white precipitate). Monitoring the reaction by TLC (petroleum ether/AcOEt 6:4) the mixture was stirred for 2 h until the starting material was completely reacted. To the mixture was then added dropwise NaBH₄ (326 mg, 8.580 mmol) dissolved in H₂O (3 ml), and the reaction mixture was stirred overnight. H₂O (30 ml) and HCl 3N (10 ml) were added, and the mixture was extracted with AcOEt (3×20 ml). The organic layer was washed with brine (15 mil), dried over anhydrous Na₂SO₄, and concentrated under reduced pressure. The resulting residue was purified by flash chromatography on Biotage™ (column: 12+M, from 5% to 55% of AcOEt in petroleum ether) to give 130 mg (~41% from 1) of mixture of 3 (70%) and 3α,12α-triacetoxy-7α,24-dihydroxy-6α-ethyl-5β-cholane (3a, 30%) as resulted from ¹H-NMR analysis. The mixture was used for the following step without further purification.

¹H-NMR (200 MHz, CDCl₃) δ: 0.66 (3H, m, 18-CH₃ of 3 and of 3a), 0.75-0.85 (m, 9H, m, 19-CH₃+21-CH₃+CH₂CH₃ of 3 and of 3a), 3.55 (2H, m, 24-CH₂OH of 3 and of 3a), 3.67 (m, 1H, 7-CH—OH of 3a), 4.52 (m, 3-CHOAc of 3 and of 3a), 4.99-5.06 (2H, m, 12-CHOAc of 3 and 3a and 7-CHOAc of 3).

3α,7α,12α-trihydroxy-6α-ethyl-5β-cholan-24-solfonate (3A)

To a solution of triphenylphosphine (270 mg, crude of previous step) in distilled CH₂Cl₂ (4 mil) under N₂ atmosphere, bromine (0.02 ml, 0.426 mmol) and imidazole (0.02 ml, 0.426 mmol) were added, and the mixture was stirred for 10'. 3 (130 mg, 0.237 mmol) diluted in distilled CH₂Cl₂ (4 mil) was then added dropwise, and the mixture was stirred until the starting material was completely reacted. CH₂Cl₂ (20 ml) was then added, and the reaction mixture was washed with H₂O (3×20 ml), brine (15 ml), dried over anhydrous Na₂SO₄, and concentrated under reduced pressure. The resulting residue was purified by flash chromatography on Biotage™ (column: 12+M, from 5% to 55% of AcOEt in petroleum ether) to give 65 mg (~45%) as mixture of 4 (70%) and 3α,12α-triacetoxy-7α,24-dihydroxy-6α-ethy-5β-cholane (4a 30%).

This mixture was then solubilized in EtOH (10 ml), Na₂SO₃ 5% in H₂O (9 ml) was added dropwise, and the reaction was stirred at 90° for 12 h. The mixture was warmed at room temperature and stirred overnight. The reaction mixture was then concentrated under reduced pressure, and the resulting residue was diluted with H₂O (15 ml), acidified with HCl 3N and extracted with CH₂Cl₂ (3×15 ml). The organic layer was washed with brine (15 ml), dried over anhydrous Na₂SO₄, and concentrated under reduced pressure. The resulting residue was then treated with NaOH 5% in H₂O (15 ml) and refluxed for 24 h. The mixture was concentrated under reduced pressure and the residue was diluted with H₂O (15 ml), washed with CH₂Cl₂ (2×15 ml), acidified with HCl 3N and extracted with AcOEt/MeOH 8:2 (3×25 ml). The organic layer was dried over anhydrous Na₂SO₄ and concentrated under reduced pressure. The resulting residue was purified by medium pressure chromatography (column: "RP-1 8 Lobar B", MeOH/H₂O 6:4, 50 psi) to give 3α,7α,12α-trihydroxy-6α-ethyl-5β-cholan-24-sulfonate sodium salt, 3A (47 mg, 93%).

Mp: >280° C.

¹H-NMR (400 MHz, CD₃OD) δ: 0.72 (3H, s, 18-CH₃), 0.90 (6H, m, 19-CH₃ and CH₃CH₂), 1.04 (3H, d, J=6.51 Hz, 21-CH₃), 1.89 (1H, m, 23-CH), 2.70 (2H, m, 24-CH₂SO₃), 3.30 (1H, m, 3-CH), 3.68 (1H, m, 7-CH), 3.98 (1H, m, 12-CH).

¹³C-NMR (100.3 MHz, CD₃OD) δ: 10.41, 11.41, 16.27, 21.20, 21.84 (2), 22.54, 26.57, 27.14, 28.03, 29.38, 32.71, 34.59, 34.63, 35.05, 35.40, 40.06, 41.40, 41.48, 45.25, 45.85, 46.63, 51.50, 69.58, 71.50, 72.40.

Example 1B

Synthesis of 3α,7α,23-trihydroxy-6a-ethyl-23(S)-methyl-24-nor-5β-cholan-23-sulfate sodium salt (2A)

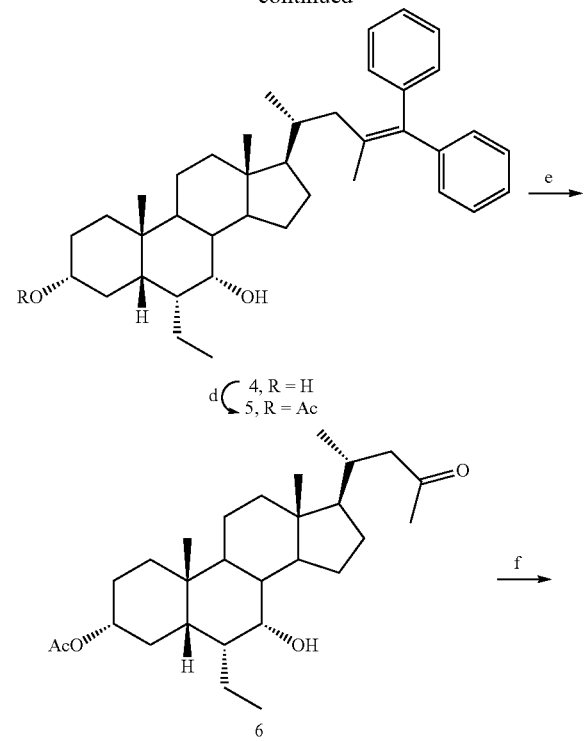

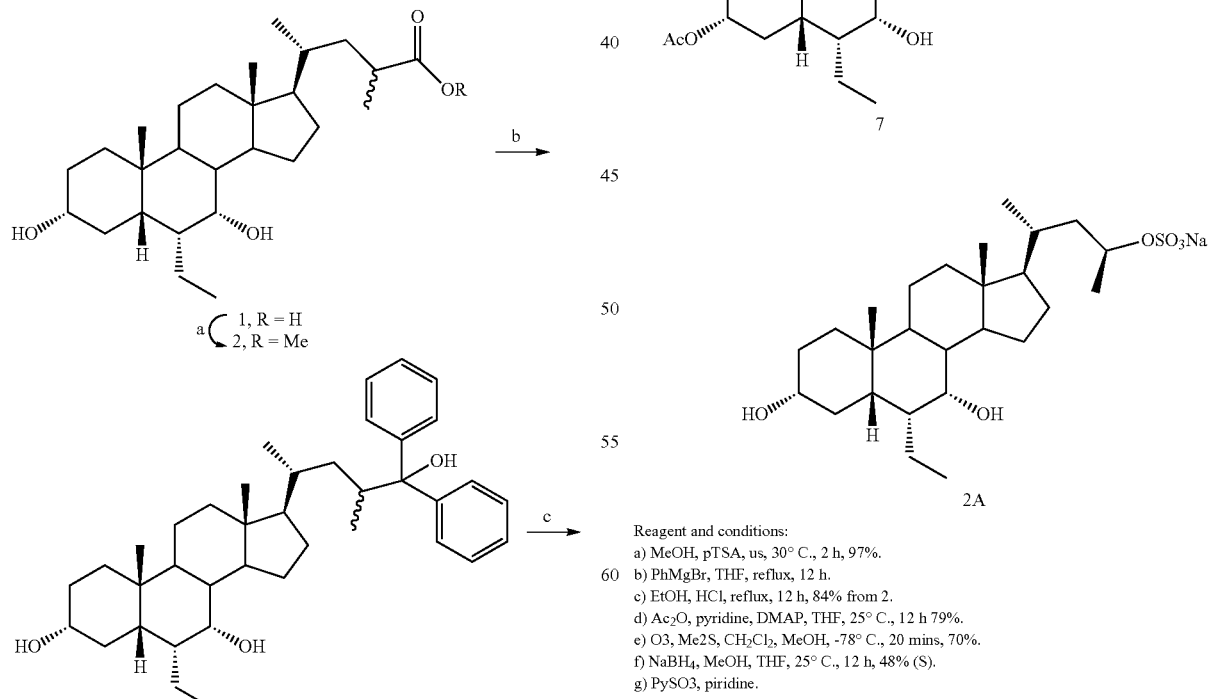

Reagent and conditions:
a) MeOH, pTSA, us, 30° C., 2 h, 97%.
b) PhMgBr, THF, reflux, 12 h.
c) EtOH, HCl, reflux, 12 h, 84% from 2.
d) Ac₂O, pyridine, DMAP, THF, 25° C., 12 h 79%.
e) O3, Me2S, CH₂Cl₂, MeOH, -78° C., 20 mins, 70%.
f) NaBH₄, MeOH, THF, 25° C., 12 h, 48% (S).
g) PySO3, piridine.
h) 5% NaOH in MeOH, 43%. Overall Yield: 9%.

Methyl 3α,7α-dihydroxy-23-methy-6α-ethyl-5β-cholan-24-oate (2)

To a solution of 1 (2.0 g, 4.6 mmol) in methanol (150 ml) p-TSA (0.2 g, 1.05 mmol) was added and the mixture was treated under ultrasound for 90'. The solvent was evaporated under reduce pressure, the residue was dissolved in CHCl$_3$ (200 ml) washed with a saturated aqueous solution of sodium bicarbonate (2×100 ml), water (100 ml) and brine (100 ml). The organic layer was dried on anhydrous sodium sulfate and evaporated to dryness to afford the methyl ester 2 (2.0 g, 97%) as white solid.

3α,7α-diihydroxy-23-methyl-6α-ethyl-5β-bisnor-cholanyldiphenylethylene(4)

To a solution of the methyl ester 2 (1.35 g, 3.01 mmol) in freshly distilled THF (15 ml) phenylmagnesiumbromide (24.1 ml, 1M in THF) was added and the resulting mixture was refluxed overnight. The solution was allowed to room temperature, a 3N hydrochloric solution (30 ml) was added dropwise and mixture was stirred for 30 min. The organic phase was separated and the aqueous one was extracted with EtOAc (3×50 ml). The combined organic layers were washed with brine (1×100 ml), dried over anhydrous sodium sulfate and evaporated to dryness under reduced pressure, to get the intermediate 3, that was used for the following step without purification. The brown crude was dissolved in a mixture of ethanol (35 ml) and 12N HCl (1 ml) and the mixture was refluxed overnight. The solvent was evaporated in vacuo, the residue was dissolved in CH$_2$Cl$_2$ (100 ml) washed with a saturated solution of sodium bicarbonate (2×60 ml), water (60 ml), brine (60 ml), dried over anhydrous sodium sulfate and evaporated under reduced pressure. The residue was purified by flash chromatography eluting with CHCl$_3$/MeOH 98:2 to afford the desired derivative 4 as white solid (1.40 g, 84% from 2).

$^1$H-NMR (CDCl$_3$) δ: 0.7 (3H, s, 18-CH$_3$), 0.85 (3H, d, J=6.5 Hz, 21-CH$_3$), 0.88-0.92 (6H, m, 19-CH$_3$+CH$_2$CH$_3$), 0.97-1.22 (6H, m), 1.23-1.52 (9H, m), 1.57-1.70 (5H, m), 1.78-1.85 (4H, m), 1.92-1.95 (1H, m), 3.40-3.42 (1H, m, 3-CH), 3.69 (1H, bs, 7-CH), 7.25-7.29 (4H, m, ArH), 7.127.23 (6H, m, ArH).

$^{13}$C-NMR (CDCl$_3$) δ: 11.6, 11.7, 17.8, 20.0, 20.6, 22.2, 23.1, 23.6, 28.4, 30.5, 33.12, 33.8, 34.8, 35.4 (2×), 39.4, 39.9, 41.1, 41.6, 42.8, 45.1, 50.4, 56.8, 70.8, 72.3, 125.8, 127.8 (4×), 128.6 (4×), 129.8 (2×), 138.8, 143.4.

3α-acetoxy-7α-hydroxy-23-methyl-6α-ethyl-5β-bisnorcholanyldiphenylethylene(5)

To a solution of 4 (1.85 g, 3.33 mmol) in freshly distilled THF (15 ml) acetic anhydride (0.35 ml, 3.66 mmol), pyridine (0.05 ml, 0.66 mmol), 4-di(methylamino)-pyridine (28 mg, 0.23 mmol) were added and the resulting mixture was stirred at room temperature overnight. The mixture was diluted with water (70 ml) and extracted with EtOAc (3×50 ml). The combined organic layers were washed with water (2×50 ml), brine (50 ml), dried over anhydrous sodium sulfate and evaporated to dryness under reduced pressure to get the desired acetylated compound 5 (1.57 g, 79%) as white solid that was used for the next step without further purification.

$^1$H-NMR (CDCl$_3$) δ: 0.65 (3H, s, 18-CH$_3$), 0.85 (3H, d, J=6.5 Hz, 21-CH$_3$), 0.87-0.92 (6H, m, 19-CH$_3$+CH$_2$CH$_3$), 0.95-1.26 (8H, m), 1.30-1.50 (6H, m), 1.52-1.70 (5H, m), 1.75 (3H, s, 24-CH$_3$), 1.79-1.97 (5H, m), 2.01 (3H, s, 3-CHOC(O)CH$_3$), 2.14-2.17 (1H, m), 3.69 (1H, bs, 7-CH), 4.52-4.57 (1H, m, 3-CH), 7.11-7.22 (6H, m, ArH), 7.25-7.29 (4H, m, ArH).

$^{13}$C-NMR (CDCl$_3$) δ: 11.6, 11.8, 17.9, 20.1, 20.7, 21.4, 22.2, 23.1, 23.7, 26.6, 28.4, 29.6, 33.1, 34.9, 35.2, 35.5, 39.5, 40.0, 41.2, 41.6, 42.9, 45.1, 50.4, 56.9, 70.7, 74.7, 125.8, 127.8 (4×), 129.5 (4×), 129.8 (2×), 134.0, 138.9, 143.5.

3α-acetoxy-7α-hydroxy-6α-ethyl-5β-cholan-23-one (6)

A solution of 5 (1.35 g, 2.26 mmol) in a mixture of dry MeOH (15 ml) and dry CH$_2$Cl$_2$ (20 ml) kept at −78° C. was ozonized until the deep blue colour was persistent for 30 min. The ozonization was then interrupted and the blue deep solution was swept with nitrogen to free the dissolved ozone. When the reaction is no more blue Me2S (0.55 ml, 7.55 mmol) was added and the solution was allowed to return to room temperature. The solvent was then removed under reduced pressure and the residue was purified by flash chromatography eluting with from 2% to 15% of EtOAc in petroleum ether, to afford the desired ketone 6 as white solid (0.7 g, 70%).

$^1$H-NMR (CDCl$_3$) δ: 0.7 (3H, s, 18-CH$_3$), 0.85-0.9 (9H, m, 19-CH$_3$+21-CH$_3$+CH$_2$CH$_3$), 1.04-1.23 (7H, m), 1.29-1.46 (8H, m), 1.58-1.72 (4H, m), 1.78-1.97 (5H, m), 2.00 (3H, s, 3-CHOC(O)CH$_3$), 2.11 (1H, s, 24-CH$_3$), 2.43-2.53 (1H, m), 3.70 (1H, bs, 7-CH), 4.48-4.59 (1H, m, 3-CH).

$^{13}$C-NMR (CDCl$_3$) δ: 11.6, 11.8, 19.7, 20.7, 21.5, 22.1, 23.1, 23.7, 26.6, 28.4, 29.6, 30.6, 32.6, 33.1, 35.1, 35.5, 39.5, 39.9, 41.1, 42.8, 45.0, 50.5, 50.9, 56.0, 70.7, 74.7, 170.7, 209.3.

3α-acetoxy-7α,23(S)-dihydroxy-6α-ethyl-5β-cholane(7)

To a stirred solution of ketone 6 (0.5 g, 1.12 mmol) in THF at 0° C. NaBH$_4$ (0.27 g, 7.17 mmol) was added in one portion and then MeOH (0.27 ml, 6.76 mmol) was added dropwise. At the end of the addition the reaction was warmed to room temperature and stirred overnight. The solvent was then evaporated to dryness, the residue was dissolved in CH$_2$Cl$_2$ and 3N HCl and stirred for 1 h. The two phases were separated, the organic layer was washed with water, brine, dried over anhydrous sodium sulphate and evaporated to dryness under reduced pressure. The oily residue, which consisted of two components as evidenced by TLC, was purified by flash chromatography (petroleum ether/EtOAc 7:3) to afford firstly the 3α-acetoxy-7α,23(S)-dihydroxy-6α-ethyl-5f3-cholane 7 (0.225 g, 48%), then the more polar 3α-acetoxy-7α,23(R)-dihydroxy-6α-ethyl-5f3-cholane (0.105 g, 23%) in a 2:1 ratio.

$^1$H-NMR (CDCl$_3$) δ: 0.7 (3H, s, 18-CH$_3$), 0.88-0.91 (6H, m, 19-CH$_3$+CH$_2$CH$_3$), 0.97 (3H, d, J=6.4 Hz, 21-CH$_3$), 1.04-1.08 (4H, m,), 1.19 (3H, d, J=6.1, 24-CH$_3$), 1.26-1.56 (12H, m), 1.53-1.71 (5H, m), 1.76-1.96 (4H, m), 2.0 (3H, s, 3-CHOC(O)CH$_3$), 3.72 (1H, bs, 7-CH), 3.79-3.95 (1H, m, 23-CH), 4.51-4.59 (1H, m, 3-CH).

$^{13}$C-NMR (CDCl$_3$) δ: 11.6, 11.8, 18.5, 20.7, 21.5, 22.1, 23.1, 23.7, 24.8, 26.6, 28.4, 29.6, 32.6, 33.1, 35.1, 35.5, 39.6, 39.9, 41.1, 42.8, 45.0, 45.8, 50.5, 56.7, 65.1, 70.7, 74.7, 170.7.

6α-ethyl-23(S)methyl-3α,7α,23-trihydroxy-24-nor-5β-cholane-23 sulfate sodium salt (2A)

To a suspension of sulfurtrioxide pyridine complex (0.1 g, 0.49 mmol) in dry pyridine (5 ml), the alcohol 7 (0.2 g, 0.49 mmol) was added and the resulting mixture was stirred at room temperature under nitrogen atmosphere for 48 h after which the solvent was evaporated under reduced pressure. The residue was dissolved in 5% NaOH in MeOH (2 ml) and stirred at room temperature overnight. The solvent was evaporated under reduced pressure, the resulting solid was in a mixture of $H_2O/CH_3OH$ (1:1) and purified by reverse phase chromatography (column RP-18 lobar B) using a mixture of $CH_3OH/H_2O$ (from 5:5 to 8:2) as mobile phase, to afford the desired sulphate, 3α,7α,23-trihydroxy-6α-ethyl-23(S)-methyl-24-nor-5β-cholan-23-sulfate sodium salt, 2A (0.11 g, 43%).

$^1$H-NMR ($CD_3OD$) δ: 0.7 (3H, s, 18-$CH_3$), 0.89-0.94 (6H, m, CH-19, $CH_2CH_3$), 1.01 (3H, d, J=6.4 Hz, 21-$CH_3$), 1.09-1.29 (4H, m,), 1.32 (3H, d, J=6.1, 24-CH3), 1.36-1.41 (5H, m), 1.47-1.61 (6H, m), 1.71-1.89 (9H, m), 2.02-2.05 (1H, m), 3.28-3.35 (1H, m, 3-CH), 3.66 (1H, bs, 7-CH), 4.54-4.58 (1H, m, 23-CH).

$^{13}$C-NMR ($CD_3OD$) δ: 12.0, 12.3, 19.4, 21.9, 22.4, 23.5, 23.7, 24.6, 29.4, 31.3, 33.5, 34.4, 34.5, 36.6, 36.7, 41.1, 41.5, 43.1, 43.8, 45.5, 46.9, 51.7, 58.1, 71.2, 73.2, 74.8.

Example 2

In Vitro TGR5 and FXR Activity

The potency and efficacy of the compounds of the invention on TGR5 receptor was evaluated using in vitro assays. Table 1 shows that compounds of the invention are potent and selective TGR5 modulators. In some aspects of the invention, the compounds are dual FXR and TGR5 agonists.

For a description of an in vitro TGR5 receptor binding assay. See, e.g., Kawamata, J. Biol. Chem 2003, Vol. 278 No. 11, p. 9435-9440). Activity on FXR was assayed by fluorescence resonance energy transfer (FRET) for recruitment of the SRC-1 peptide to human FXR using a cell-free ELiSA. See, Blanchard et al. WO 00/37077. Luciferase activity was determined in CHO cells stably expressing hTGR5 or transiently cotransfected with a hTGR5 expression vector and a cAMP-responsive element (CRE)-driven luciferase reporter gene. Some of the compounds were further submitted to a luciferase reporter assay to score for their capacity to activate the nuclear bile acid receptor FXR.

The following materials and methods were used, for example, to determine the data in Table 1.

Plasmids

The NIH Mammalian Gene Collection clone MGC:40597 (also named pCMVSPORT6/hTGR5 or pTGR5) and pcDNA3.1(+) were obtained from Invitrogen (Carlsbad, Calif.). pCRE-Luc and pCMVβ were obtained from Clontech (Palo Alto, Calif.). pCMX-hFXR and pCMX-mRXRα were kind gifts from Dr. David J. Mangelsdorf (Howard Hughes Medical Institute, University of Texas Southwestern Medical Center). pEcREx7-Luc was a kind gift from Dr. Richard A. Heyman (X-ceptor Therapeutics, CA).

Cell Culture

Chinese hamster ovary (CHO) cells, NCI-H716 cells, Hep3B cells and COS1 cells were obtained from American Type Culture Collection (Manassas, Va.). Cell culture medium, serum and supplements were from Invitrogen or

TABLE 1

Potency and Efficacy of Compounds of the Invention on FXR and TGR5 Receptors

| Compound (Reference Standard) | Alphascreen Assay hFXR (CDCA = 8-25 μM) $EC_{50}$ (μM) | FRET (cAMP) NCI-H716 hTGR5 (LCA = 4-8 μM) $EC_{50}$ (μM) | Transactivation Assay hTGR5 (LCA = 1-6 μM) $EC_{50}$ (μM) | FRET-cAMP on TGR5 overexpressing HEH293 cells hTGR5 (LCA = 0.3-5 μM) $EC_{50}$ (μM) |
|---|---|---|---|---|
| 2A | 0.145 ± 0.05 | 1.6 ± 0.3 | 1.2 (LCA = 6.2) | 0.025 (LCA = 0.3) |
| 3A | 7 ± 3 | 0.7 ± 0.2 | 0.6 (LCA = 6.2) | 0.011 (LCA = 0.3) |

| Cmpd no | Chemical Structure | | TGR5 EC50 | TGR5 efficacy |
|---|---|---|---|---|
| 6A | JMC2008 37 | 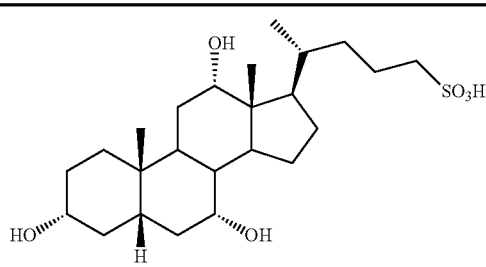 | 1.00 μM | 103 |
| 7A | JMC2008 41 | 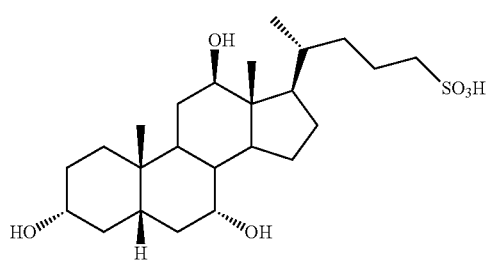 [SMILES: C[C@H](CCCS(=O)(=O)O)[C@H]1CCC2C3C(C[C@@H](O)[C@@]21C)[C@@]1(C)CC[C@@H](O)C[C@H]1C[C@H]3O] | 5.02 μM | 109 |

Sigma-Aldrich. All CHO cells were maintained in minimum essential medium α (α-MEM) supplemented with 10% (v/v) fetal bovine serum (FBS) and 100 µM nonessential amino acids (NEAA). NCI-H716 cells were maintained in suspension in RPMI-1640 supplemented with 10% (v/v) FBS, 10 mM HEPES and 1 mM sodium pyruvate. Hep3B cells were maintained in Eagle's medium supplemented with 10% (v/v) FBS and 1001 µM NEAA. COS1 cells were maintained in Dulbecco's modified Eagle's medium (DMEM) supplemented with 10% (v/v) FBS. All cell culture medium was supplemented with 100 units/ml penicillin and 100 µg/ml streptomycin sulfate. Cells were grown at 37° C. in an atmosphere of 5% CO2, passed every 2-6 days and freshly plated for each experiment.

Transient Transfections

CHO cells were plated in 96-well plates at a density of 3.5×104 cells/well, cultured for 24 h, and then transfected with 150 ng of human (h) TGR5 expression plasmid (pCMVSPORT6/hTGR5) and 100 ng of cAMP-responsive element (CRE)-driven luciferase reporter plasmid (pCRE-Luc) in each well using Lipofectamine 2000 reagent (Invitrogen) according to the manufacturer's instructions. After 6 h incubation, cells were washed once with phosphate-buffered saline (PBS) and medium was exchanged for DMEM containing 0.1% (w/v) bovine serum albumin (BSA). After incubation for another 18 h, cells were treated for 5 h with different concentrations of each compound in fresh DMEM containing 0.1% (w/v) BSA. After treatment, the cells were lysed with 50 µl of lysis buffer (25 mM Tris-Cl (pH7.6), 2 mM EDTA, 1 mM dithiothreitol (DTT), 10% (v/v) glycerol and 1% (v/v) triton X-100) by a freeze-thaw cycle and subjected to luciferase assays as described below.

COS1 cells were plated in 96-well plates at a density of 2.5×104 cells/well in DMEM supplemented with 10% (v/v) charcoal-stripped FBS, cultured for 24 h, and then transfected with 25 ng of hFXR expression plasmid (pCMX-hFXR), 25 ng of mouse (m) retinoid X receptor α (RXRα) expression plasmid (pCMX-mRXRa), 50 ng of reporter plasmid (pEcREx7-Luc) and 50 ng of pCMVβ as internal control in each well, using the Lipofectamine 2000 reagent. After 24 h, cells were washed twice with PBS and treated with different concentrations of each compound in fresh DMEM supplemented with 10% (v/v) charcoal-stripped FBS for 24 h. After treatment, the cells were lysed with 50 µl of lysis buffer by a freeze-thaw cycle and subjected to both luciferase and β-galactosidase assays as described below. Normalized luciferase values were determined by dividing the luciferase activity by the β-galactosidase activity.

Luciferase and β-Galactosidase Assays

For luciferase assays, 20 µl of cell lysate was mixed with 100 µl of luciferase reaction buffer [235 µM luciferine, 265 µM ATP and 135 µM coenzyme A (CoA)] and luminescence was determined with CentroXS3 LB960 (Berthold Technologies, Bad Wildbad, Germany). For β-galactosidase assays, 10 µl of cell lysate was mixed with 100 µl of Buffer Z [60 mM Na2HPO4, 10 mM KCl, 1 mM MgSO4, 50 mM β-mercaptoethanol and 0.75 mg/ml o-nitrophenyl-β-D-galactopyranoside (ONPG)] and incubated at 37° C. for 0.5-3 h. Reactions were stopped by adding 50 µl of Stop buffer (1M Na2CO3) and the optical density at 420 nm was determined.

Establishing CHO Cells Stably Expressing Human TGR5 (CHO-TGR5 Cells)

CHO cells were transfected with 3.8 µg of hTGR5 expression plasmid (pCMVSPORT6/hTGR5), 3.8 µg of CRE-driven luciferase reporter plasmid (pCRE-Luc) and 0.4 µg of neomycin-resistant gene expression plasmid [pcDNA3.1(+)] using Lipofectamine 2000. The transfectants were selected with 400 µg/ml G418 sulfate and single clones were grown in 96-well plate, independently. TGR5-expressing CHO cell lines were screened by LCA treatments, followed by luciferase assays.

cAMP Production Analysis

NCI-H716 cells were plated in 96-well plates coated with 0.75 mg/ml Matrigel (BD Biosciences) according to manufacturer's instructions just prior to use, at a density of 6×104 cells/well in DMEM supplemented with 10% (v/v) FBS, 100 units/ml penicillin and 100 µg/ml streptomycin sulfate, and cultured for 24 h, which allowed cell adhesion to the bottom of the plate. CHO-TGR5 cells were plated in 96-well plates at a density of 3.5×104 cells/well in α-MEM supplemented with 10% (v/v) FBS, 100 µM NEAA, 100 units/ml penicillin and 100 µg of streptomycin sulfate, and cultured for 24 h. The cells were washed twice with PBS and medium was exchanged for cAMP assay medium [DMEM containing 0.1% (w/v) BSA and 0.5 mM 3-isobutyl-1-methylxanthine (IBMX)]. After incubation for 30 minutes at 37° C. the cells were treated with each compound in fresh cAMP assay medium for 30 minutes. After treatment, medium was discarded and cAMP amounts were determined using cAMP-Screen kit (Applied Biosystems, Foster City, Calif.) according to manufacturer's instructions.

50% Effective Concentrations (EC50) and Efficacy Determination

Assays were performed in triplicate or quadruplicate for each condition. EC50 values were determined by probit analysis. Efficacy was determined by calculating percentages of 10 µM LCA value for TGR5 agonist study and 10 µM 6α-Et-CDCA value for FXR agonist study, respectively. After subtracting the average value of the basal (vehicle-treated) condition, values were applied to EC50 and/or efficacy determinations. Calculation of average EC50 and comparison of the EC50 between different compounds were done after transformation to logarithms.

Statistical Analysis

Statistical analysis was performed by Student's t-test and p<0.05 was considered statistically significant.

Example 3

Metabolic Activities of Compounds of the Invention in a Diet-Induced Obesity Mouse Model The goal of the study is to define whether TGR5 agonists (oleanolic acid (OA) or compound of the invention (for example, a "test compound")) correct the development of obesity and associated insulin-resistance in vivo. To test this possibility, OA/test compound are administered via food administration for 16 weeks to male C57BL6J mice that were previously subjected for 10 weeks to a high fat diet.

II—Protocol

In a previous study, OA was observed as a selective TGR5 agonist that did not cause food aversion. Animals treated with a dose of 100 mg/kg/day of OA showed, however, some signs of toxicity, whereas a lower dose was well tolerated. Therefore, OA is administered at the dose of 50 mg/kg/d in this study.

In vitro studies have identified compounds of the invention as potent and selective TGR5 ligands. No problems with toxicity are expected with compounds of the invention, which are administered at ~50-fold lower concentration.

For this study, 48 male C57BL6J mice (5 weeks of age) are divided in two groups: one group of 24 (group 1, 2&3)

animals receives chow diet whereas the other group of 24 receives a high fat diet for a period of 10 weeks (group 4, 5 & 6). The animals are then analyzed during a period of 16 weeks. Five groups of 10 animals are assigned as follows:
1: chow diet
2: chow diet+OA 50 mg/kg/day
3: chow diet+test compound e.g., 30 mg/kg/day
4: high fat diet
5: high fat diet+OA 50 mg/kg/day
6: high fat diet+test compound e.g., 30 mg/kg/day
During the entire study, body weight and food intake are monitored twice weekly.

Week-2: Body composition is analyzed, for all groups, by dual energy X-ray absorptiometry (dexascan).

Week-1: Serum levels of transaminases, glucose, triglycerides, cholesterol, HDL-C, LDL-C and insulin are measured in all groups after a fasting period of 12 h and mice are then placed on the diets as indicated (Day 0).

Week 2: Serum levels of transaminases, glucose, triglycerides, cholesterol, HDL-C, LDL-C and insulin are measured in all groups after a fasting period of 12 h (Day 14).

Week 4: Glucose tolerance is determined by subjecting all the animals to an intraperitoneal glucose tolerance test (IPGTT). Animals are fasted for 12 h prior to this test. Nocturnal energy expenditure of groups 1, 4, 5 and 6 (chow diet, high fat diet and high fat diet OA/test compound are measured by indirect calorimetry.

Week 8: Body weight composition is again analyzed by dexascan for all groups. Serum levels of transaminases, glucose, triglycerides, cholesterol, HDL-C, LDL-C and insulin are measured in all groups after a fasting period of 12 h (Day 56).

Week 9: Circadian activity of groups 4, 5 and 6 (high fat diet fed mice) is studied during a period of 30 h.

Week 10: Measurement of blood pressure and heart rate is performed on groups 4, 5 and 6.

Week 11: Rectal temperature of all animals is measured at room temperature at 10:00 am.
Circadian activity measurement is performed on groups 1, 2, 3 and 4.

Week 12: Glucose tolerance is analyzed by performing an intraperitoneal glucose tolerance test (IPGTT) on groups 4, 5 and 6. During the IPGTT, blood is also collected to analyze insulin levels. Animals are fasted 12 h prior to these tests. Feces are collected in all groups over a 24 h time period and fecal lipids content is measured.

Week 16: Cold test is performed on all animals by measuring body temperature of animals exposed to 4° C.

Three days later, animals are sacrificed. At sacrifice, blood is collected and analyzed for: plasma lipids (TC, TG, HDL-C, FFAs); liver functions (ALAT, ASAT, alkaline Pase, γ-GT); glucose and insulin; lipoprotein profiles of selected groups of plasma (size-exclusion chromatography).

Liver, small intestine, adipose tissues (WAT and BAT), pancreas, heart and muscle are collected, weighed and kept for further analyses including: standard histology (HE staining, succinate dehydrogenase staining, oil-red-O staining and cell morphology); tissue lipid content; electron microscopy on BAT and muscle to analyze mitochondria; RNA isolation for expression studies of selected genes involved in metabolism and energy homeostasis by quantitative RT-PCR; Protein extraction for the study of post-translational modifications such as acetylation of proteins of interest (e.g. PGC-1α).

III—Detailed Procedures
A—Animal Procedure and Diets
Animals Housing and Handling Mice are group housed (5 animals/cage) in specific pathogen-free conditions with a 12 h:12 h (on at 7:00) light-dark cycle, in a temperature (20-22° C.) and humidity controlled vivarium, according to the European Community specifications. Animals are allowed free access to water and food.

Drinking Water

Chemical composition of the tap water is regularly analyzed to verify the absence of potential toxic substances at the Institut d'Hydrologie, ULP, Strasbourg. Drinking water is treated with HCl and $HClO_4$ to maintain pH between 5 and 5.5 and chlorin concentration between 5 and 6 ppm.

Diet

The standard rodent chow diet is obtained from UAR and the high fat diet is obtained from Research Diet. Mice are fed, either with chow diet (16% protein, 3% fat, 5% fiber, 5% ash) or with high fat diet (20% protein, 20% carbohydrate, 60% fat). Oleanolic acid and test compound were mixed with either powdered chow diet or either powdered high fat diet in the following proportions: 0.5 g of OA/kg of food for the 50 mg/kg/day treatment and 0.08 g of test compound/kg of food for the 10 mg/kg/day treatment. Pellets are then reconstituted. Control groups receive food pellets without test compound or OA. Due to the consistency of the high fat diet, no water is added in the mix with OA. In the case of the chow diet, which is harder to reconstitute, a minimal amount of water is added to the powder to reconstitute pellets, which are then air-dried. New batches of food are prepared weekly.

Blood Collection

Blood is collected either from the retro-orbital sinus under anesthesia or from the tail vein.

Anesthesia

For the dexa scanning experiment, animals are anesthesized with a mixture of ketamine (200 mg/kg)/Xylasine (10 mg/kg) administered by intra-peritoneal injection.

For the venipuncture, animals are anesthesized by inhalation of an isoflurane-02 mixture.

B-Biochemistry

The tests are performed with an Olympus AU-400 automated laboratory work station using commercial reagents (Olympus).

Analysts of Lipids and Lipoproteins

Serum triglycerides, total and HDL cholesterol are determined by enzymatic assays. Serum HDL cholesterol content are determined after precipitation of apo B-containing lipoproteins with phosphotungstic acid/Mg (e.g., Roche Diagnostics, Mannheim, Germany). Free fatty acids level are determined with a kit from Wako (e.g., Neuss, Germany) as specified by the provider.

Metabolic and Endocrine Exploration

Blood glucose concentration is measured by a Precision Q.I.D analyzer (e.g., Medisense system), using Medisense Precis electrodes (e.g., Abbot Laboratories, Medisense products, Bedford, USA). This method is validated, by comparing Precision Q.I.D analyzer values with classical glucose measurements. The Precision Q.I.D method was chosen since it requires a minimal amount of blood and can hence be employed for multiple measurements such as during an IPGTT. Plasma insulin (e.g., Mercodia, Uppsala, Sweden) is determined by ELISA according to the manufacturer's specifications.

C-Metabolic Testing
Lipoprotein Profiles

Lipoprotein profiles are obtained by fast protein liquid chromatography, allowing separation of the three major lipoprotein classes VLDL, LDL, and HDL.

Intraperitoneal Glucose Tolerance Test (IPGTT)—Oral Glucose Tolerance Test

IPGTT is performed in mice which are fasted overnight (12 h). Mice are either injected intraperitoneally (IPGTT) with a solution of 20% glucose in sterile saline (0.9% NaCl) at a dose of 2 g glucose/kg body weight. Blood is collected from the tail vein, for glucose and insulin monitoring, prior and 15, 30, 45, 75, 90, 120, 150, 180 min after administration of the glucose solution. The incremental area of the glucose curve is calculated as a measure of insulin sensitivity, whereas the corresponding insulin levels indicate insulin secretory reserves.

Energy Expenditure

Energy expenditure is evaluated through indirect calorimetry by measuring oxygen consumption with the Oxymax apparatus (e.g., Columbus Instruments, Columbus, Ohio) during 12 h. This system consists of an open circuit with air coming in and out of plastic cages (one mouse per cage). Animals are allowed free access to food and water. A very precise $CO_2$ and $O_2$ sensor measures the difference in $O_2$ and $CO_2$ concentrations in both air volumes, which gives the amount of oxygen consumed in a period of time given that the air flow of air coming in the cage is constant. The data coming out of the apparatus is processed in a connected computer, analyzed, and shown in an exportable Excel file. The values are expressed as $ml \cdot kg^{-1} \cdot h^{-1}$, which is commonly known as the $VO_2$.

Determination of Body Fat Content by Dexa Scanning

The Dexa analyses are performed by the ultra high resolution PIXIMUS Series Densitometer (0.18×0.18 mm pixels, GE Medical Systems, Madison, Wis., USA). Bone mineral density (BMD in $g/cm^2$) and body composition are determined by using the PIXIMUS software (version 1.4×, GE Medical Systems).

D-Non-Invasive Blood Pressure Measurement and Pulse

The Visitech BP-2000 Blood Pressure Analysis System is a computer-automated tail'cuff system that is used for taking multiple measurements on 4 awake mice simultaneously without operator intervention. The mice are contained in individual dark chambers on a heated platform with their tails threaded through a tail cuff. The system measures blood pressure by determining the cuff pressure at which the blood flow to the tail is eliminated. A photoelectric sensor detects the specimen's pulse. The system generates results that have been shown to correspond closely with mean intra-arterial pressure measured simultaneously in the carotid artery. This allows reproducible values of systolic blood pressure and heart beat rate to be obtained. This requires training of the animals for one week in the system.

E—Circadian Activity

Spontaneous locomotor activity is measured using individual boxes, each composed with a sliding floor, a detachable cage, and equipped with infra-red captors allowing measurement of ambulatory locomotor activity and rears. Boxes are linked to a computer using an electronic interface (e.g., Imetronic, Pessac, France). Mice are tested for 32 hours in order to measure habituation to the apparatus as well as nocturnal and diurnal activities. The quantity of water consumed is measured during the test period using an automated lickometer.

Example 4

Physico-Chemical Properties

Water Solubility

Solid compound (BA) was suspended in 5 ml of 0.1 M HCl. The saturated solutions, after incubation for 1 week, were filtered on a Millipore filter (0.22 μpm) and the concentration of BA is measured by HPLC-ESI-MS/MS using Cl 8 column (150 mm×2 mm i.d., 4 μm) and mobile phases of water containing 15 mM acetic acid pH 5 and acetonitrile. The flow rate was 150 μl/min. The mass spectrometry acquisition was performed in the multiple reaction monitoring mode using the ESI source in negative ionization. Water solubility was expressed as μmol/liter.

The water solubility was measured for the insoluble protonated species of carboxylated bile acids at a pH 1. Sulphate and sulphonate compounds 3A and 2A are ionized even at low pH and in physiological conditions are always soluble in all biological fluids.

TABLE 2

Physicochemical properties of the studied analogues and natural occurring BA.

| Bile Acid | Ws[a] (μM) | CMC[b] 0.15M Na+ (mM) | $ST_{CMC}$[c] Dyne/cm | $LogP_{A-}$[d] | Albumin Binding [e] (%) |
|---|---|---|---|---|---|
| CDCA | 32 | 3.2 | 45.5 | 2.2 | 93 |
| UDCA | 7.5 | 6.0 | 50.5 | 2.2 | 94 |
| CA | 273* | 11* | — | 1.1* | 50* |
| TCDCA | hs | 3.0* | — | 0.9* | 70* |
| TUDCA | hs | 2.2* | — | 1.1* | 67* |
| 6MUDCA | 28* | 4.2* | — | 0.3* | 80* |
| 3A | hs | 2.8 | 43.4 | 0.7 | 81 |
| 2A | hs | Not available | Not available | 2.3 | 97 |

[a]Ws: water solubility refers to BA as protonated species and therefore not evaluated for 3A, 2A, TCDCA, and TUDCA which are highly soluble (hs).
[b]CMC: Critical Micellar Concentration determined in 0.15M NaCl water solution.
[c]$ST_{CMC}$: Surface Tension at CMC in 0.15M NaCl water solution.
[d]$LogP_{A-}$: 1-octanol-water partition coefficient of the studied bile acids as ionized species.
*values from literature.

Critical Micellar (Concentration (CMC)

The detergency i.e. the tendency to form micelles was evaluated for charged molecules which are soluble in water as Sodium salt (2 unit up the pKa). The critical micellar concentration (CMC) was determined by surface tension (ST) measurements using a maximum bubble-pressure method which give surface tension values slightly affected by potential impurities like static methods are. The tensiometer was a Sensadyne 6000 (Chem-Dyne Research Corp., Milwaukee, Wis.) equipped with two glass probes of 0.5 and 4.0 mm diameters connected to a source of nitrogen. The bubble frequency was 1 bubble/second in distilled water at 26° C. (P=2.7 atm) and the calibration was made with double-distilled water and methanol. The surface tension of BA sodium salts solutions in NaCl 0.15 M was measured at various concentrations inside the 0.13-50 mM range. The surface tension values were plotted against the logarithm of the bile salt concentration; the regression lines corresponding to the two parts of the curve (monomeric and micellar phases) were calculated using the method of least squares, and the intersection of the lines was taken as the CMC value. From the ST vs concentration curves the value of the surface tension at the CMC (equilibrium between monomers and multimers species) was also calculated giving information about the detergency power which is related to the size of the micelles with associate surface tension lowering capacity.

The CMC was evaluated by surface tension measurements in non equilibrium conditions i.e. in conditions that impurities slightly affect the surface tension results (FIG. 1). Compound 3A presents a high surface tension lowering capacity with a CMC of 2.8 mM. The behaviour of the ST vs concentration suggests the formation of relatively large aggregate with consistent detergency.

Octanol/Water Partition Coefficient

Since the sulphate and sulphonated analogues are always ionised at all pH values the octanol/water partition coefficient was measured for all molecules in ionized form, 1-Octanol/water partition coefficient (log P) was evaluated using a conventional shake-flask procedure. The experiments were carried out on 0.1 mM bile salt solution buffered at pH 8 with 0.1 M phosphate buffer to ensure complete ionization of the BA, the log P values refer to the BA in the ionized form, not to the protonated species, and the initial concentration of each BA was below its own CMC value. The aqueous buffer was previously pre-saturated with 1-octanol, 5 ml of 1-octanol pre-saturated with water was then added and the samples were left to equilibrate for 2 weeks under continuous stirring at room temperature After centrifugation the two phases were carefully separated. BA concentration in the water phase was measured with HPLC-ESI-MS/MS using C18 column (150 mm×2 mm i.d., 4 µm) and, as mobile phases, water containing 15 mM acetic acid pH 5 and acetonitrile. The flow rate was 150 µal/min and the column was maintained at 45° C. The mass spectrometry acquisition was performed in the multiple reaction monitoring mode using the ESI source in negative ionization.

The 1-octanol/water partition coefficient was calculated for the ionized species to facilitate the comparison between the carboxyl and sulphate bile acids since the latter did not protonate even at very low pH value.

Albumin Binding

The extent of albumin binding was evaluated by equilibrium dialysis at a fixed BA-albumin ratio. BA was dissolved at a concentration of 100 µM in 5% bovine serum albumin-saline solution (pH 7.2) and left to stand for 24 h at 25° C. Two milliliters of this solution was dialyzed in cellulose sacs having a molecular weight cut-off of 12-14,000 against 25 ml of saline solution. The system was equilibrated by mechanical gently shaking for 72 h at 25° C. BA concentrations of the dialyzed solution (corresponding to the free unbound fraction) and of the starting solution were determined with HPLC-ESI-MS/MS in the same conditions of the previous analysis. The percent of albumin binding was calculate from the initial BA concentration and from the unbound concentration in the dialyzed fraction. Data are reported in the Table 2. All these compounds never less present an albumin binding compatible with a relatively fast hepatic uptake, similarly to natural occurring BA. Accordingly different kinetics (slower) of the liver uptake is expected.

Example 5

In Vitro Metabolic Stability in Human Stool Culture

Stability to Intestinal Bacteria.
7a-dehydroxylation.

Homogenized fresh human stools (500 mg) were transferred into sterile vials to which 5 mL of sterilized chopped meat-glucose medium (Scott Lab., Fiskville, R.I.) was added. BA were then added at a final concentration of 0.05 mM. Vials were incubated at 37° C.; then, at 0, 1, 2, 4, 8 and 24 h after the addition of the BA, the reaction was stopped with 150 µL of 30% KOH. The samples were centrifuged at 3500 rpm for 10 min; from the supernatant the BA were isolated by C-18 solid-phase extraction and analyzed by TLC and HPLC-ES-MS/MS.

Thin-layer chromatography (TLC), utilizing silica gel 0.25 mm thickness plates (Merck, Darmstat, Germany), was employed as the first screening test. The solvent system used for the separation of conjugated BA was composed of propionic acid/isoamyl acetate/water/N-propanol (3:4:1:2, v/v/v/v; solvent 1), and that of the unconjugated BA was acetic acid/carbon tetrachloride/isopropyl ether/isoamyl acetate/water/N-propanol/benzene (1:4:6:8:2:2, v/v/v/v/v/v; solvent II). Separated BA were revealed with 5% phosphomolybdic acid ethanol solution.

Figure 2:
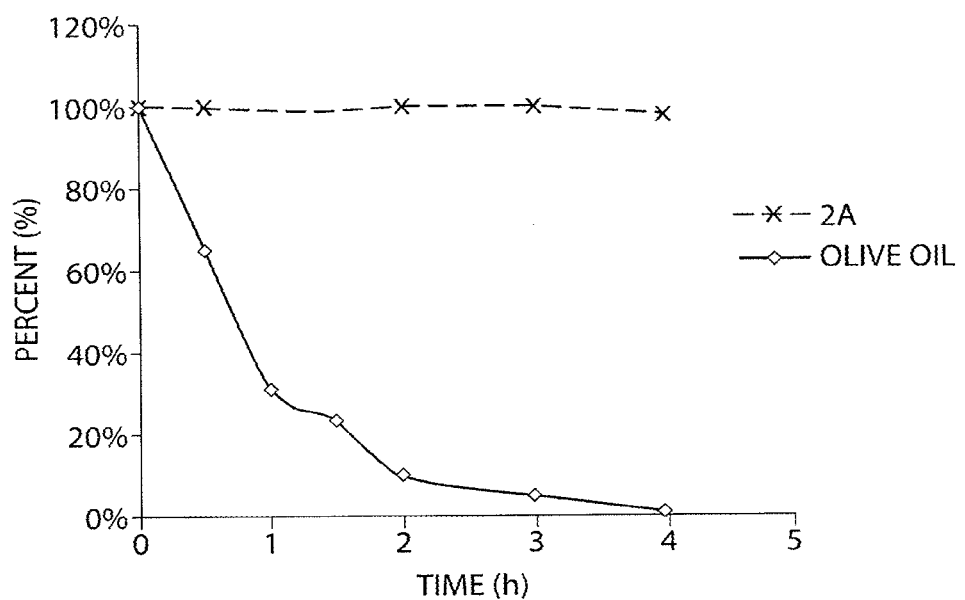
FIG. 2 is a graph that depicts that metabolic stability of 2A in simulated pancreatic fluid.

All the studied analogues are very stable when incubated in human stool cultures and even after 24 hour more than 85% of the compounds can be recovered unmodified as reported in FIG. 2. On the contrary the reference natural analogue CDCA presents an half-life time of almost one hour and after 8 hours of incubation is almost completely metabolized (7-dehydroxylated) to form lithocholic acid. After also long time incubation for all 6 ethyl analogues the 7 dehydroxylation and the intermediate formation of a 7 oxo derivative is practically abolished.

Side Chain Stability

According to the first results the side chain is not modified by the intestinal bacteria enzymatic activities. These data suggest that the presence of the ethyl group in the 6 position protects the 7 hydroxyl group toward oxidation or removal by steric hindrance. In addition all the analogues are very stable also for side chain metabolism. The side chain ester bond of sulphate analogue 2A is quite stable in the human stool culture. The sulphonate analogue 3A is also very stable. No minor metabolites have been found by HPLC-ES-MS/MS. These data suggest that in the lower intestinal content in presence of anaerobic bacteria these analogues are stable.

Example 6

In Vitro Metabolic Stability in Simulated Duodenal/Pancreatic Fluid (USP Specification)

This study has been performed for 2A since it contains an ester bond in the side chain and the aim was to verify the stability in presence of esterase enzymes like present in duodenal and pancreatic juice. Simulated pancreatic fluid was prepared by dissolving 10 g/L Pancreatin (Sigma P8096: pancreatin from porcine pancreas, activity 1×USP specifications) in 0.05M phosphate buffer, pH=7.2±0.1. Then, 4-mL aliquots of the simulated pancreatic fluid were added of 50 pM of the studied BA and incubated for different times (0, 30, 60, 90, 120, 180 and 240 min) at 37° C. After incubation, a 2-mL aliquot of each solution was added with 2 mL of 0.1M NaOH and subjected to bile acids extraction by SPE and analysis by thin-layer chromatography and mass spectrometry as described above. FIG. 2 shows the metabolic stability of 2A in simulated pancreatic fluid. Olive oil was used as a reference as reported in the USP protocol. The compound is very stable (see FIG. 2) and the ester bond (sulphate) in 2A is not hydrolyzed by pancreatic esterases suggesting an high stability in human duodenal and upper intestine content.

Example 7

Biliary Secretion and Metabolism of Compound 3A in Bile-Fistula Rat after Duodenal (Id) and Femoral (iv) Administration Aim and Rationale The structural modification of the new analogues could affect their hepatic uptake, hepatic transports and secretion and intestinal absorption. Therefore the knowledge of the biliary secretion after both iv and id administration together their metabolism is a key point in the candidate selection for additional studies.

To evaluate the mode and efficiency of the intestinal absorption the analogues were administered both intravenously (femoral infusion) and orally (duodenal infusion) at the same dose and their biliary secretion rate was evaluated in bile fistula rat model. The differences in the area under the curve of the biliary secretion vs time between iv and id administration account of its intestinal absorption and give information about its bioavailability.

Choleretic Effect

Duodenal Infusion

The bile fistula rat model was developed at the University of Bologna Lab facilities. The compound 3A was administered at a dose of 1 µmol/kg/min (1 hour infusion) to a rat group via duodenal infusion (id). Rat have a bile fistula to collect bile samples at different times before and during the infusion. For duodenal infusion experiment 3 rats (250±10 g) were treated. Bile samples were collected every 15 minutes for four hours. In addition, 3 control rats were treated with saline solution under the same conditions for times and sampling (duodenal control rats).

Figure 3:
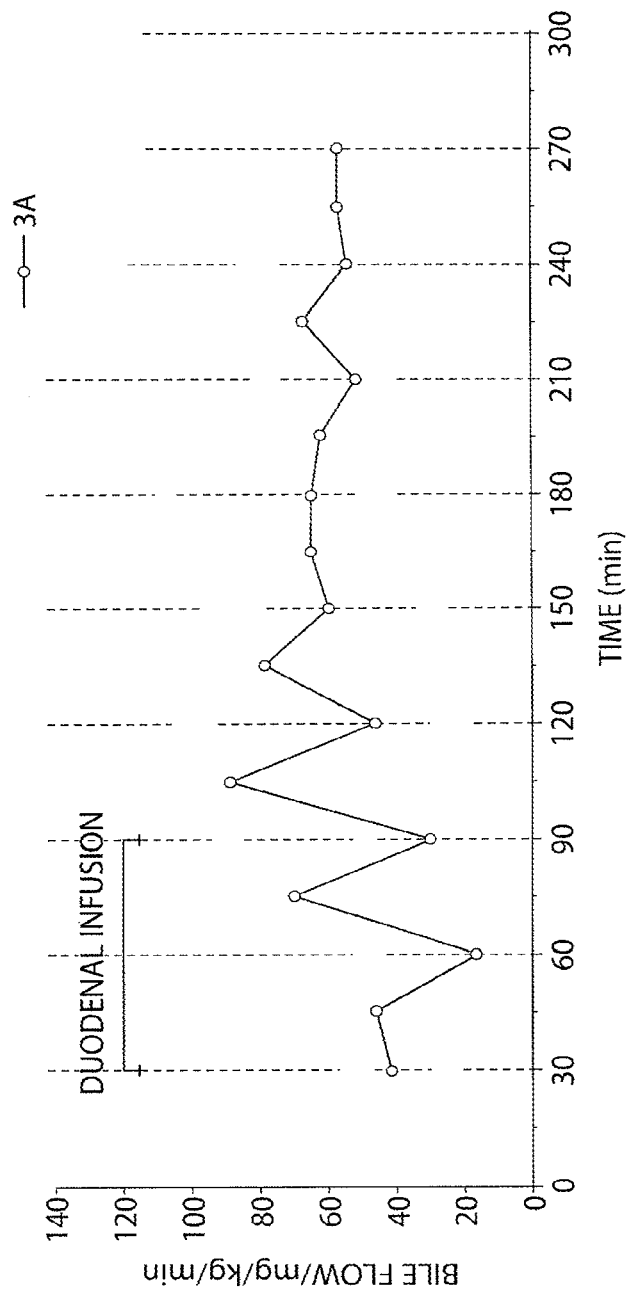
FIG. 3 is a bile flow chart for a duodenal infusion experiment performed using 3A.

FIG. 3 shows bile flow during sample collection (one animal). Duodenal infusion starts after 30 min baseline bile collection and continues for one hour. Compound 3A presents a moderate choleretic effect.

Intravenous Infusion

Figure 4:
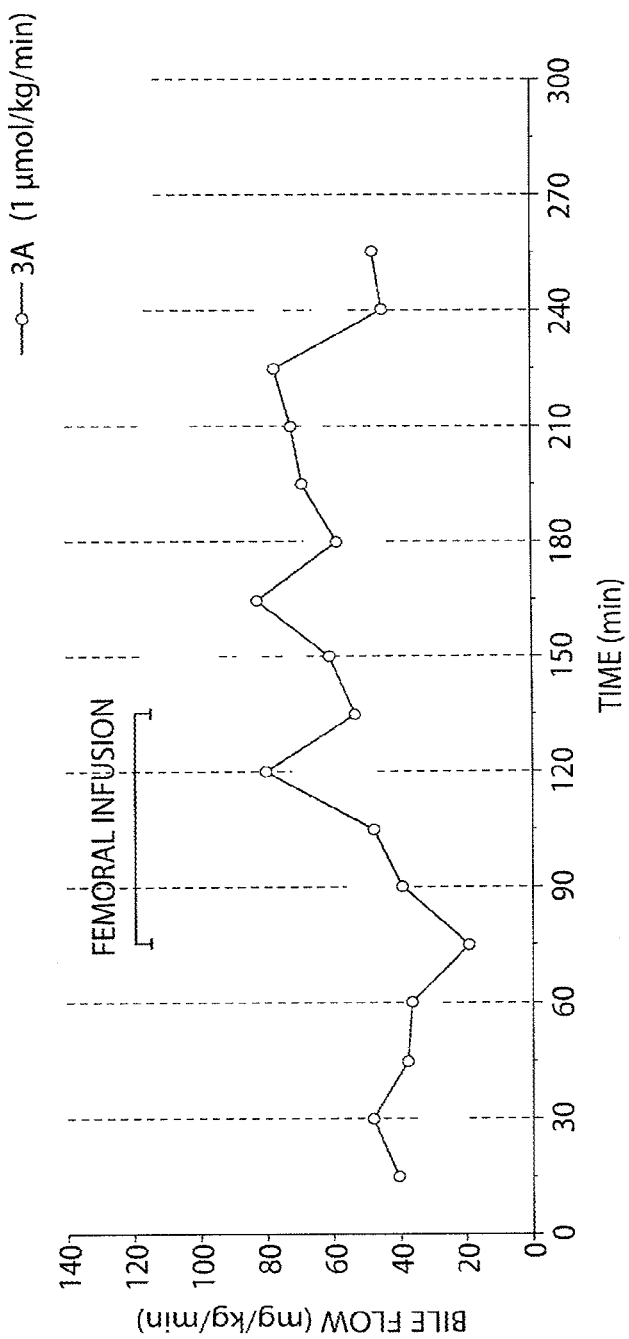
FIG. 4 is a bile flow chart for a femoral infusion experiment performed using 3A.

For femoral infusion experiment, 3 rats were treated. FIG. 4 shows bile flow during the study. Femoral infusion starts after 75 minutes of steady-state and continues for 60 min. Bile samples were collected every 15 minutes for four hours. In addition, 3 rats were treated with saline solution under the same conditions for times and sampling (femoral control rats).

Compound 3A presents a moderate choleretic effect and similar to that obtained in the id experiment Biliary Secretion of the Administered Analogues Bile samples collected during the iv and id experiments were analyzed to determine the biliary secretion of the administered analogues and their metabolites.

HPLC-ES-MS/MS analysis. Stock solutions of each compound in methanol at 1 mmol/L (with the exception of UPF 1212 at 350 µmol/L) were prepared and working solutions were prepared by diluting appropriate volumes of the primary solution. Methanol and acetonitrile was of HPLC-grade purity. Ammonia was 30% and acetic acid was 99.8%. All reagents were obtained from Carlo Erba Reagents. HPLC-grade water was prepared by a Milli-Q system.

Sample Preparation

Rat bile samples were brought to room temperature, briefly stirred, and diluted 1:100 v/v (bile samples from duodenal orinfusion) and 1:100 or 1:200 v/v (bile samples from femoral infusion) with 15 mM ammonium acetate buffer (pH=5.0):acetonitrile=70:30 (v/v). Final solution was transferred in autosampler vials, and 10 µL was injected into the chromatographic column.

HPLC-ESI-MS/MS Method

Bile rat samples were analyzed by liquid chromatography-tandem mass spectrometry (HPLC-MS:MS) using electrospray (ESI) source in negative ionization mode. For liquid chromatography a Waters Alliance 2695 separation module coupled with autosampler was used. Autosampler was maintained at 7° C. Separation was performed on a Synergi Hydro-RP Cl, column (150×2.0 mm i.d., 4 µm particle size), protected by a SecurityGuard ODS 4×2.0 mm i.d. precolumn, both supplied from Phenomenex. Analyte was eluted using 15 mM ammonium acetate buffer (pH=5.00) as mobile phase A and acetonitrile as mobile phase B. Mobile phase B was increased from 30% to 64% in 10 min, then to 100% in 10 min, and held constant for 10 min. Flow rate was 150 µL/min and the column was maintained at 45° C. The column effluent was introduced into ESI source connected to a triple quadruple mass spectrometer (Quattro-LC, Micromass) operating in Multiple Reaction Monitoring (MRM) acquisition mode. Nitrogen was used as nebulizer gas at 90 L/h flow rate and as desolvation gas at 930 L/h. Ion source block and desolvation temperatures were set respectively to 80° C. and 180° C. Capillary voltage was 3.0 kV. MassLynx software version 4.0 was used for data acquisition and processing. In addition, using mass spectrometry both in single MS or tandem MS/MS configuration experiments were performed to identify metabolites.

Quantification

A 5-point calibration curve was daily prepared and injected in duplicate. Calibration samples were obtained in the 0.1 to 25 µmol/L concentration range prepared in mobile phase. Linear calibration curve parameters were obtained from the plot of the analyte peak area versus analyte concentration using a least squares regression analysis (weight=1/x$^2$). Correlation coefficients were ≥0.989.

Pharmacokinetic (Biliary Secretion) of the Administered Analogues: iv Versus id Comparison The data refer to the secretion rate of the analogues recovered in bile as such after duodenal and femoral infusion at a dose of 1 umol/Kg/min. Major and minor metabolites are reported later. Table 3 shows compound 3A concentration and secretion values obtained from bile rat samples collected during the duodenal infusion (1 h ranging from 75 to 135 min). Table 4 shows compound 3A concentration and secretion values obtained from bile rat samples collected during the femoral infusion (1 h ranging from 75 to 135 min)

TABLE 3

| | 3A | |
| --- | --- | --- |
| Time (min) | Conc. (mmol/L) | Secretion (µmol/kg/min) |
| 90 | n.d.[b] | —[a] |
| 120 | 0.37 | 0.026 |
| 150 | 0.90 | 0.079 |
| 180 | 1.3 | 0.101 |
| 210 | 0.95 | 0.061 |
| 240 | 0.70 | 0.043 |
| 270 | 0.58 | 0.039 |
| 300 | 0.51 | 0.029 |

[a]—: not calculated
[b]n.d.: not detected

TABLE 4

| | 3A | |
| --- | --- | --- |
| Time (min) | Conc. (mmol/L) | Secretion (μmol/kg/min) |
| 75 | n.d.[b] | —[a] |
| 90 | 2.6 | 0.105 |
| 120 | 7.3 | 0.588 |
| 150 | 7.5 | 0.463 |
| 180 | 6.2 | 0.363 |
| 210 | 3.4 | 0.247 |
| 240 | 1 | 0.045 |

[a]—: not calculated
[b]n.d.: not detected

Figure 5:
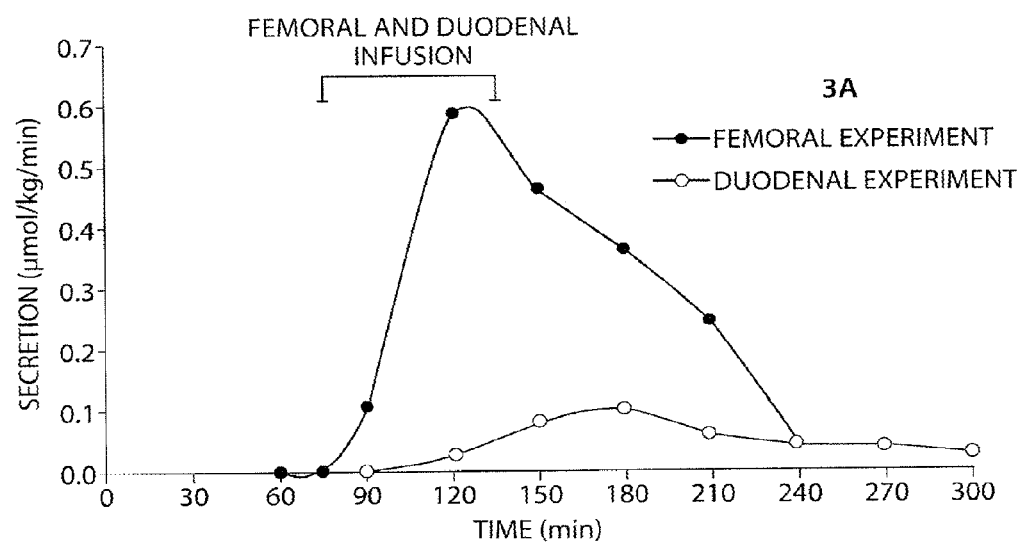
FIG. 5 is a graph that depicts secretion rates verses time in femoral and duodenal infusion experiments performed using 3A.

The biliary secretion of compound 3A (sulphonated analogue) after iv administration is very efficient and the compound is almost completely recovered in bile. The kinetic profile indicates that the analogue is efficiently taken up by the liver and secreted in bile almost as such without hepatic metabolism (FIG. 5). On the contrary after id administration the recovery in bile is much lower than the recovery after iv administration suggesting that the compound is poorly absorbed by the intestine (FIG. 5). According to the physicochemical properties, this compound is poorly absorbed by passive diffusion mechanism (low Log P=0.71) and active mechanism does not seem to be involved. The presence of three hydroxyl groups renders the molecule on one side efficiently taken up by the liver and secreted into bile but on the other side poorly absorbed by the intestine.

Example 8

Hepatic Metabolism

For a preliminary screening the search of the possible metabolites has been performed on the basis of the expected compounds according to previous experiments and data and to the structure and physicochemical properties of the studied analogues.

Figure 6:
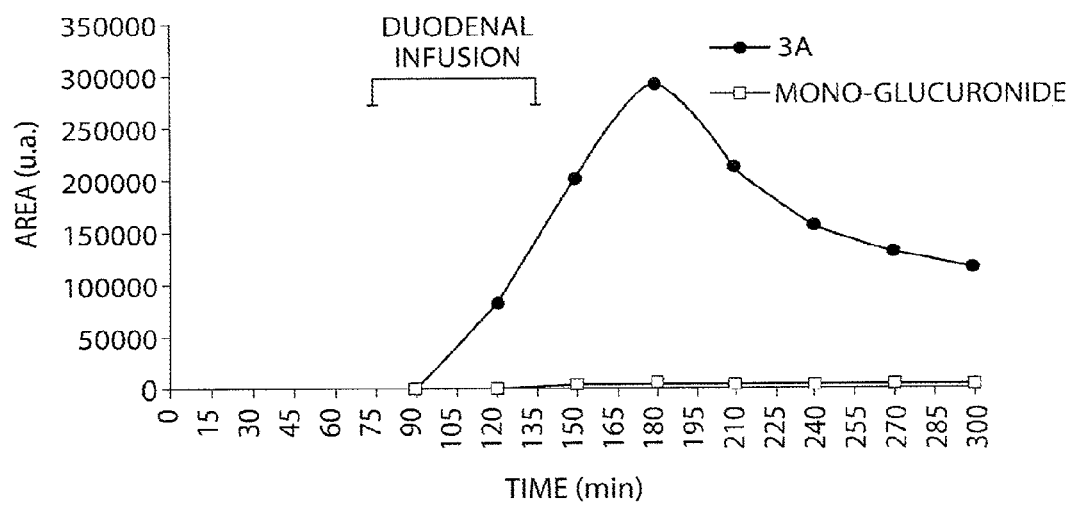
FIGS. 6 and 7 are graphs that shows 3A and its main metabolite identified in bile using mass spectrometry in a duodenal infusion experiment. Data are reported as absolute area values.
Figure 7:
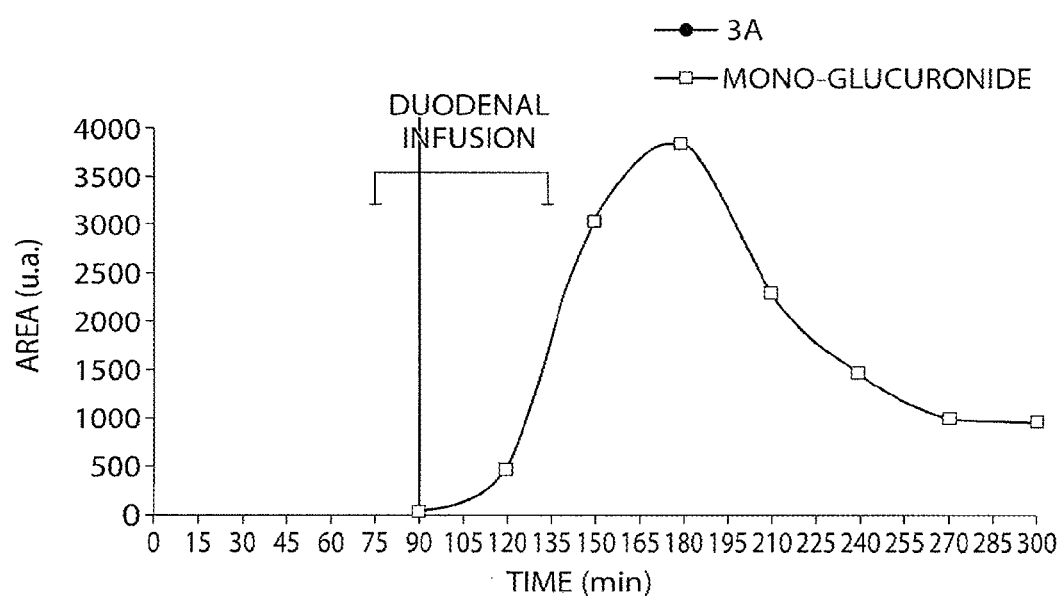

Compound 3A is not metabolized by the liver or by the intestine and once taken up by the liver is secreted in bile unmodified with a fast kinetic resulting in a low hepatic residence time. When administered via id is poorly absorbed by the intestine and also in this case is not metabolized. Due to its relatively high hydrophylicity (low Log P) and to the presence of the sulphonate group and three hydroxyls the compound 3A is enough polar to be secreted in bile as such but too much polar to be absorbed by passive mechanism by the intestine. FIG. 6 shows compound 3A and its main metabolite identified in bile using mass spectrometry in the di experiment. Data are reported as absolute area values. FIG. 7 shows a zoom display of FIG. 6.

Example 9

Compound In Vitro Toxicity on HepG2 Cell

Compounds of the invention were evaluated for cytotoxicity using standard methods known in the art. Specifically, cytotoxicity was evaluated using HEPG2 cells and monitoring ATP decrease and determining the EC50 value. Both compound 3A and 2A showed an EC50>1000 mM.

| Compound | HepG2 cell Cytotoxicity ATP decrease EC50 (μM) |
| --- | --- |
| Staurosporine | 15 |
| Tamoxifen | 47 |
| LCA | 84 |
| CDCA | 650 |
| UDCA | >1000 |
| CA | >1000 |
| 3A | >1000 |
| 2A | >1000 |

Example 10

NR Selectivity Assays

The selectivity of compounds of the invention was evaluated using assay methods known in the art. Specifically, the following assay methods were used:
FXR and LXR: Coactivator Recruitment (alphascreen);
TGR5: cAMP level on human intestinal cell line (NCI-H716);
PXR: Ligands Competition assay (Binding Assay)
CAR: Coactivator Recruitment (Lanthascreen)

| Compound (Ref standard) | FXR (CDCA = 10-20 μM) EC50 (μM) | TGR5 (LCA = 4-8 μM) EC50 (μM) | LXRα (T0901317 = 0.08 μM) EC50 (μM) | PXR (SR-12183 = 0.013 μM) EC50 (μM) | CAR (CITCO = 0.005 μM) EC50 (μM) | PPARδ (0.004 μM) EC50 (μM) | VDR (0.005 μM) EC50 (μM) |
| --- | --- | --- | --- | --- | --- | --- | --- |
| CDCA | 20 | 30 | No activity | >250 | >250 | No activity | No activity |
| LCA | No activity | 4-8 | No activity | 23 | No activity | No activity | No activity |
| CA | No activity | 30 | No activity | No activity | No activity | No activity | No activity |
| UDCA | >150 | No activity | No activity | >250 | >250 | No activity | No activity |
| 2A | 0.14 | 1.6 | No activity | 21 | 84 | No activity | No activity |
| 3A | 7 | 0.7 | No activity | 150 | >250 | No activity | No activity |

Example 11

Metabolic Activity of Compound 3A in a Diet-Induced Obesity Mouse Model

The goal of the study was to assess the therapeutic potency of compound 3A in a mouse model of diet-induced obesity. Compound 3A was administered via food administration for 16 weeks to male C57BL6J mice that were previously subjected for 10 weeks to a high fat diet.

II—Protocol

Compound 3A was administered for this study.

For this study, male C57BL6J mice (5 weeks of age) were divided in 2 groups: one group of animals received chow diet to control the onset of obesity, one group of animals received a high fat diet. Compound 3A was tested on the animals that received the high fat diet (HFD). The animals are then analyzed during a period of 13 weeks. The groups were as follows:
1: chow diet
2: high fat diet
3: high fat diet+3A During the entire study, body weight and food intake were monitored twice weekly.

The period for the onset of obesity was 10 weeks. At the end of the 10 weeks, body composition was analyzed by dual energy X-ray absorptiometry (dexascan) and serum levels of transaminases, glucose, triglycerides, cholesterol, HDL-C, LDL-C and insulin were measured.

After 1 week: Compound was administered.

After 3 weeks: Blood collection. Serum levels of transaminases, glucose, triglycerides, cholesterol, HDL-C, LDL-C and insulin were measured in all groups after a fasting period of 12 h.

After 2 weeks: Body weight composition was again analyzed by dexascan for all groups.

After 2 weeks: Nocturnal energy expenditure was measured by indirect calorimetry and actimetry.

After 2 weeks: Glucose tolerance was determined by subjecting all the animals to an intraperitoneal glucose tolerance test (IPGTT). Animals were fasted for 12 h prior to this test.

After 2 weeks: Animals were sacrificed. At sacrifice, blood was collected and analyzed for: plasma lipids (TC, TG, HDL-C, FFAs); liver functions (ALAT, ASAT, alkaline Pase, γ-GT); glucose and insulin; lipoprotein profiles of selected groups of plasma (size-exclusion chromatography).

Liver, small intestine, adipose tissues (WAT and BAT), pancreas, heart and muscle were collected, weighed and kept for further analyses including: standard histology (HE staining, succinate dehydrogenase staining, oil-red-O staining and cell morphology); tissue lipid content; electron microscopy on BAT and muscle to analyze mitochondria; RNA isolation for expression studies of selected genes involved in metabolism and energy homeostasis by quantitative RT-PCR; Protein extraction for the study of post-translational modifications such as acetylation of proteins of interest (e.g. PGC-1α).

III—Detailed Procedures

A—Animal Procedure and Diets

Animals Housing and Handling

Mice were group housed (5 animals/cage) in specific pathogen-free conditions with a 12 h: 12 h (on at 7:00) light-dark cycle, in a temperature (20-22° C.) and humidity controlled vivarium, according to the European Community specifications. Animals were allowed free access to water and food.

Drinking Water

Chemical composition of the tap water was regularly analyzed to verify the absence of potential toxic substances at the Institut d'Hydrologie, ULP, Strasbourg. Drinking water was treated with HCl and $HClO_4$ to maintain pH between 5 and 5.5 and chlorin concentration between 5 and 6 ppm.

Diet

The standard rodent chow diet was obtained from UAR and the high fat diet was obtained from Research Diet. Mice were fed, either with chow diet (16% protein, 3% fat, 5% fiber, 5% ash) or with high fat diet (20% protein, 20% carbohydrate, 60% fat). Compound 3A was mixed with powdered high fat diet. Pellets were then reconstituted. The HFD control group received food pellets without compound 3A. In the case of the chow diet, which is harder to reconstitute, a minimal amount of water was added to the powder to reconstitute pellets, which are then air-dried. New batches of food were prepared weekly.

Blood Collection

Blood was collected either from the retro-orbital sinus under anesthesia or from the tail vein.

Anesthesia

For the dexa scanning experiment, animals were anesthesized with a mixture of ketamine (200 mg/kg)/Xylasine (10 mg/kg) administered by intra-peritoneal injection.

For the venipuncture, animals were anesthesized by inhalation of an isoflurane-02 mixture.

B-Biochemistry

The tests were performed with an Olympus AU-400 automated laboratory work station using commercial reagents (Olympus).

Analysis of Lipids and Lipoproteins

Serum triglycerides, total and HDL cholesterol were determined by enzymatic assays. Serum HDL cholesterol content were determined after precipitation of apo B-containing lipoproteins with phosphotungstic acid/Mg (e.g., Roche Diagnostics, Mannheim, Germany). Free fatty acids level were determined with a kit from Wako (e.g., Neuss, Germany) as specified by the provider.

Metabolic and Endocrine Exploration

Blood glucose concentration was measured by a Precision Q.I.D analyzer (e.g., Medisense system), using Medisense Precis electrodes (e.g., Abbot Laboratories, Medisense products, Bedford, USA). This method was validated, by comparing Precision Q.I.D analyzer values with classical glucose measurements. The Precision Q.I.D method was chosen since it requires a minimal amount of blood and can hence be employed for multiple measurements such as during an IPGTT. Plasma insulin (e.g., Mercodia, Uppsala, Sweden) were determined by ELISA according to the manufacturer's specifications.

C-Metabolic Testing

Lipoprotein Profiles

Lipoprotein profiles were obtained by fast protein liquid chromatography, allowing separation of the three major lipoprotein classes VLDL, LDL, and HDL.

Intraperitoneal Glucose Tolerance Test (IPGTT)—Oral Glucose Tolerance Lest

IPGTT was performed in mice which were fasted overnight (12 h). Mice were either injected intraperitoneally (IPGTT) with a solution of 20% glucose in sterile saline (0.9% NaCl) at a dose of 2 g glucose/kg body weight. Blood was collected from the tail vein, for glucose and insulin monitoring, prior and 15, 30, 45, 75, 90, 120, 150, 180 min after administration of the glucose solution. The incremental area of the glucose curve was calculated as a measure of insulin sensitivity, whereas the corresponding insulin levels indicate insulin secretory reserves.

Energy Expenditure

Energy expenditure was evaluated through indirect calorimetry by measuring oxygen consumption with the Oxymax apparatus (e.g., Columbus Instruments, Columbus, Ohio) during 12 h. This system consists of an open circuit with air coming in and out of plastic cages (one mouse per cage). Animals were allowed free access to food and water. A very precise $CO_2$ and $O_2$ sensor measures the difference in $O_2$ and $CO_2$ concentrations in both air volumes, which gives the amount of oxygen consumed in a period of time given that the air flow of air coming in the cage is constant. The data coming out of the apparatus was processed in a connected computer, analyzed, and shown in an exportable Excel file. The values were expressed as $ml \cdot kg^{-1} \cdot h^{-1}$, which is commonly known as the $VO_2$.

Determination of Body Fat Content by Dexa Scanning

The Dexa analyses were performed by the ultra high resolution PIXIMUS Series Densitometer (0.18×0.18 mm pixels, GE Medical Systems, Madison, Wis., USA). Bone mineral density (BMD in $g/cm^2$) and body composition were determined by using the PIXIMUS software (version 1.4×, GE Medical Systems).

D-Non-Invasive Blood Pressure Measurement and Pulse

The Visitech BP-2000 Blood Pressure Analysis System is a computer-automated tail' cuff system that is used for taking multiple measurements on 4 awake mice simultaneously without operator intervention. The mice were contained in individual dark chambers on a heated platform with their tails threaded through a tail cuff. The system measures blood pressure by determining the cuff pressure at which the blood flow to the tail is eliminated. A photoelectric sensor detects the specimen's pulse. The system generates results that have been shown to correspond closely with mean intra-arterial pressure measured simultaneously in the carotid artery. This allows reproducible values of systolic blood pressure and heart beat rate to be obtained. This requires training of the animals for one week in the system.

E—Circadian Activity

Spontaneous locomotor activity was measured using individual boxes, each composed with a sliding floor, a detachable cage, and equipped with infra-red captors allowing measurement of ambulatory locomotor activity and rears. Boxes were linked to a computer using an electronic interface (e.g., Imetronic, Pessac, France). Mice were tested for 32 hours in order to measure habituation to the apparatus as well as nocturnal and diurnal activities. The quantity of water consumed was measured during the test period using an automated lickometer.

Figure 8:
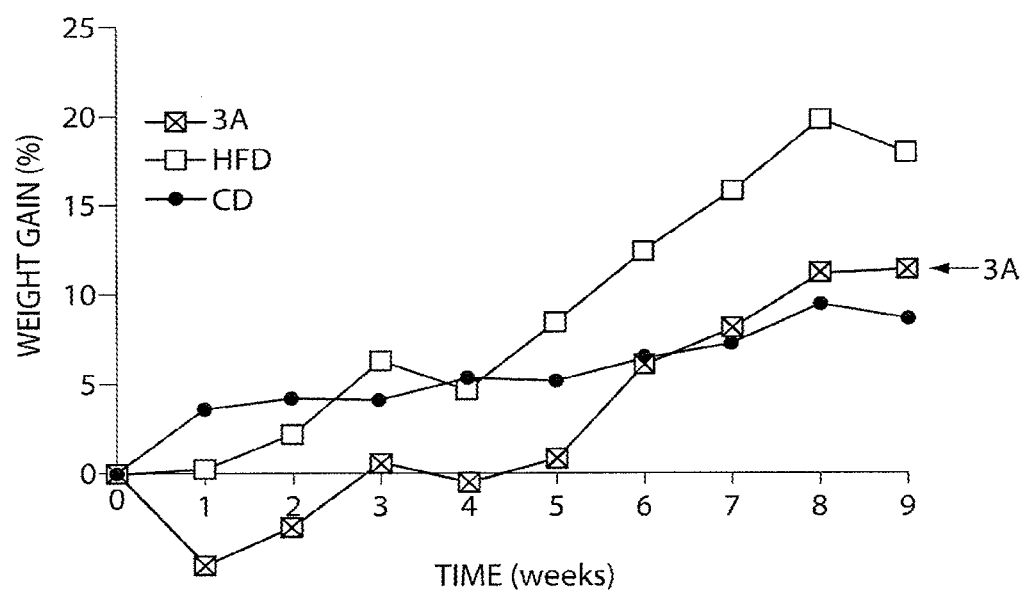
FIG. 8 is a graph that shows the evolution of weigh gain after treatment (%) (Example 11).
Figure 9:
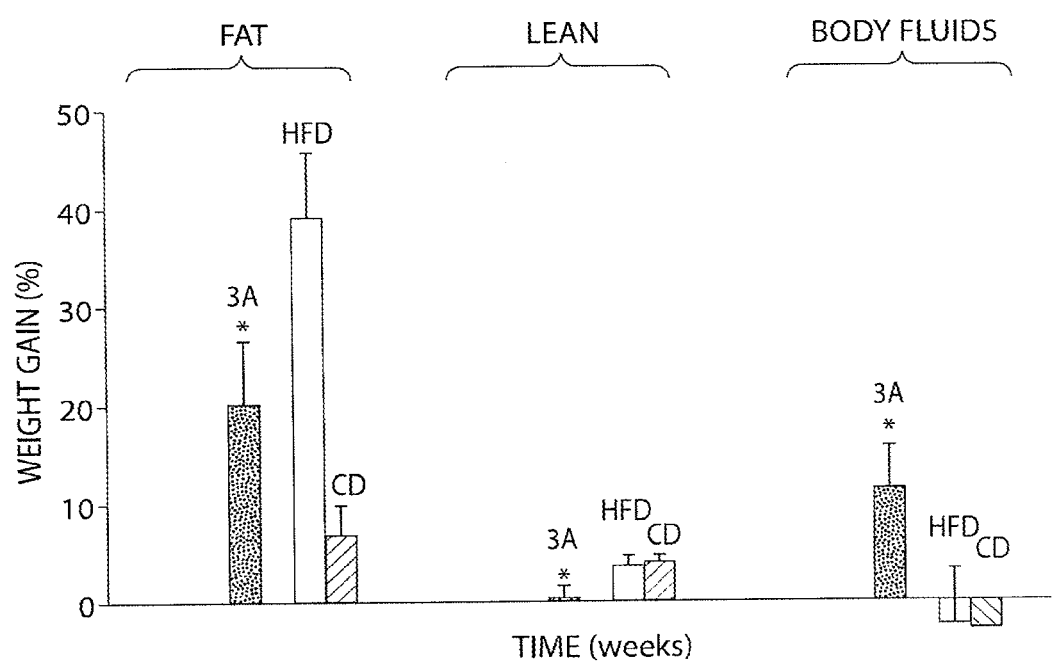
FIG. 9 is a series of bar graphs the evolution of body composition after treatment (%) 5 weeks after treatment (Example 11).
Figure 10A:
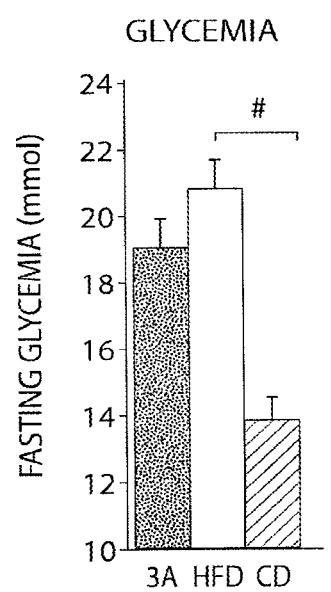
FIGS. 10A, 10B and 10C show an assessment of glucose homeostasis for compound 3A.
Figure 10B:
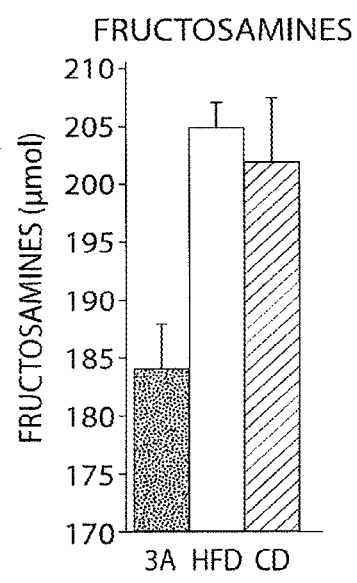
Figure 10C:
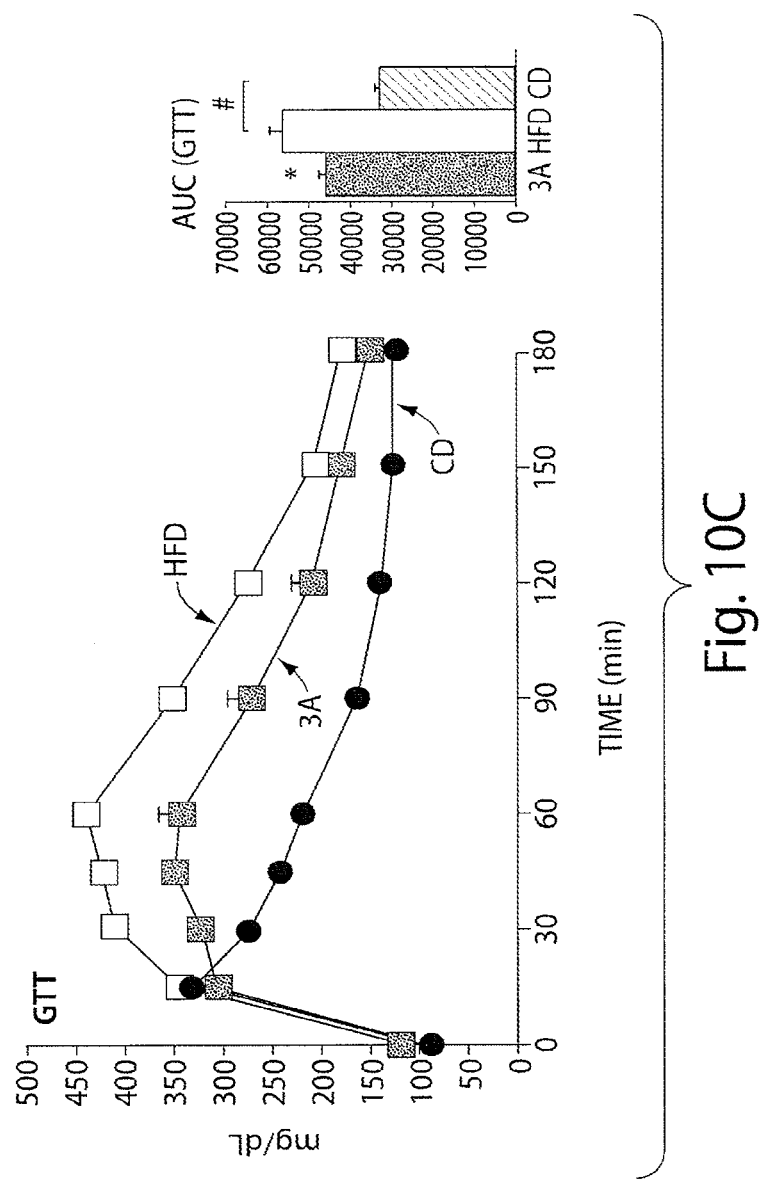

The results of this study are shown in FIGS. 8, 9, and 10A, 10B and 10C. FIG. 8 shows the evolution of weigh gain after treatment (%). The graph shows % weight gain (0, 5, 10, 15, 20, 25) verses time (0-9 weeks). Body weight gain is blunted in the HF-fed mice treated with compound 3A. FIG. 9 shows the evolution of body composition after treatment (%) 5 weeks after treatment. Graphs with % weight gain are shown for fat, lean and body fluid measurements. Compound 3A reduces fat gain upon HFD. FIGS. 10A, 10B, and 10C show an assessment of glucose homeostasis for compound 3A. FIG. 10A shows glycemia 3 weeks after treatment. Specifically, FIG. 10A is a bar graph that compares 3 groups of mice (x-axis): mice on HFD administered compound 3A (first bar), mice on a HFD (second bar), and mice on a chow diet (third bar) and their fasting glycemia (y-axis) mmol/l at 10, 12, 14, 16, 18, 20, and 22. FIG. 10B shows fructosamines 3 weeks after treatment. Specifically, FIG. 10B is a bar graph that compares 3 groups of mice (x-axis): mice on HFD administered compound 3A (first bar), mice on a HFD (second bar), and mice on a chow diet (third bar) and their fructosamines (y-axis) micromole at 170, 175, 180, 185, 195, 200, 205, and 210. FIG. 10C shows the results of a glucose tolerance test 9 weeks after treatment. Specifically, FIG. 10C is a graph that compares 3 groups of mice: mice on HFD administered compound 3A, mice on a HFD, and mice on a chow diet. The y-axis shows the amount in mg/dL (0, 50, 100, 150, 200, 250, 300, 350, 400, 450, 500) and the x-axis shows time in minutes 0, 30, 60, 90, 120, 150, and 180.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims. It will be understood by those skilled in the art that various changes in form and details may be made therein without departing from the scope of the invention encompassed by the appended claims.

What is claimed:

1. A compound of formula A:

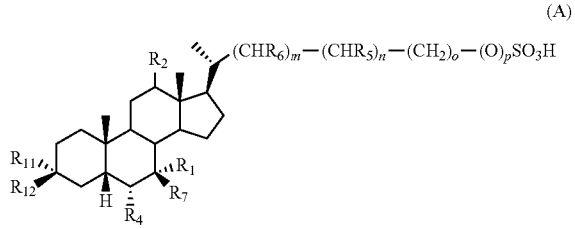

(A)

or a salt thereof, wherein:

$R_1$ is hydrogen, hydroxy, substituted or unsubstituted alkyl, or halogen;

$R_2$ is hydrogen or a-hydroxy;

$R_4$ is substituted or unsubstituted alkyl, or halogen;

$R_5$ is hydrogen, unsubstituted alkyl, or aryl;

$R_6$ is hydrogen, unsubstituted or substituted alkyl, or $R_5$ and $R_6$ taken together with the carbons to which they are attached form a ring of size 3, 4, 5, or 6 atoms;

$R_7$ is hydrogen, substituted or unsubstituted alkyl, or hydroxy;

$R_{11}$ is hydroxyl, $OSO_3H$, $OSO_3^-$, $OCOCH_3$, $OPO_3H$, $OPO_3^{2-}$ or hydrogen;

$R_{12}$ is hydroxyl, $OSO_3H$, $OSO_3^-$, $OCOCH_3$, $OPO_3H$, $OPO_3^{2-}$ or hydrogen, or taken together $R_{11}$ and $R_{12}$ form a carbonyl;

m is 0, 1, or 2;

n is 0 or 1;

o is 0 or 1; and p is 1; provided that m+n+o=3 or 4 and when m+n+o=3, then at least one of $R_5$ and $R_6$ is not hydrogen.

2. A pharmaceutical composition comprising a compound according to claim 1 and at least one pharmaceutically acceptable excipient.

* * * * *